US012653415B2

(12) United States Patent
Grouchy et al.

(10) Patent No.: US 12,653,415 B2
(45) **Date of Patent: *Jun. 16, 2026**

(54) METHOD AND SYSTEM TO ASSESS DISEASE USING PHASE SPACE TOMOGRAPHY AND MACHINE LEARNING

(71) Applicant: Analytics For Life Inc., Toronto (CA)

(72) Inventors: Paul Grouchy, Toronto (CA); Meng Lei, North York (CA); Ian Shadforth, Morrisville, NC (US); Sunny Gupta, Belleville (CA); Timothy William Fawcett Burton, Toronto (CA); Shyamlal Ramchandani, Kingston (CA)

(73) Assignee: Analytics For Life Inc., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/438,858

(22) Filed: Feb. 12, 2024

(65) Prior Publication Data

US 2024/0423494 A1     Dec. 26, 2024

Related U.S. Application Data

(63) Continuation of application No. 16/232,586, filed on Dec. 26, 2018, now Pat. No. 11,918,333.

(Continued)

(51) Int. Cl.
A61B 5/0536     (2021.01)
A61B 5/00     (2006.01)
(Continued)

(52) U.S. Cl.
CPC ............ A61B 5/0536 (2013.01); A61B 5/026 (2013.01); A61B 5/316 (2021.01); A61B 5/339 (2021.01);
(Continued)

(58) Field of Classification Search
CPC ....... Y02A 90/10; A61B 5/7267; A61B 5/349; A61B 5/7264; A61B 5/02007;
(Continued)

(56) References Cited

U.S. PATENT DOCUMENTS 5,769,074 A * 6/1998 Barnhill .............. G01N 33/573
600/300
2007/0032728 A1 2/2007 Longhini
(Continued)

FOREIGN PATENT DOCUMENTS

JP        2001070269      * 3/2001    ............. A61B 5/296
WO   WO-2017221221 A1 * 12/2017    ......... A61B 5/02007

OTHER PUBLICATIONS

Xiong et al., "Myocardial Perfusion Analysis in Cardiac Computed Tomography Angiographic Images at Rest", 2016, Med Image Anal (Year: 2016).*

(Continued)

*Primary Examiner* — Zhiyu Lu
(74) *Attorney, Agent, or Firm* — Meunier Carlin & Curfman LLC

(57) ABSTRACT

The exemplified intrinsic phase space tomography methods and systems facilitate the analysis and evaluation of complex, quasi-periodic system by generating computed phase-space tomographic images as a representation of the dynamics of the quasi-periodic cardiac systems. The computed phase-space tomographic images can be presented to a physician to assist in the assessment of presence or non-presence of disease. In some embodiments, the phase space tomographic images are used as input to a trained neural network classifier configured to assess for presence or non-presence of significant coronary artery disease.

20 Claims, 31 Drawing Sheets

Related U.S. Application Data

(60) Provisional application No. 62/612,130, filed on Dec. 29, 2017.

(51) Int. Cl.

| | |
|---|---|
| *A61B 5/026* | (2006.01) |
| *A61B 5/316* | (2021.01) |
| *A61B 5/339* | (2021.01) |
| *G06T 3/4007* | (2024.01) |
| *G06T 11/00* | (2006.01) |
| *G06T 11/60* | (2006.01) |
| *G06T 17/20* | (2006.01) |

(52) U.S. Cl.
CPC .......... *A61B 5/7267* (2013.01); *G06T 3/4007* (2013.01); *G06T 11/006* (2013.01); *G06T 11/60* (2013.01); *G06T 17/20* (2013.01); *G06T 2200/08* (2013.01); *G06T 2210/24* (2013.01); *G06T 2210/41* (2013.01)

(58) Field of Classification Search
CPC ....... A61B 5/021; A61B 5/316; A61B 5/4842; A61B 5/0205; A61B 5/7275; A61B 5/7282; A61B 5/02108; A61B 5/02405; A61B 5/02416; A61B 5/02427; A61B 5/02433; A61B 5/0245; A61B 5/14551; A61B 5/318; A61B 5/7239; A61B 5/7246; A61B 5/7203; A61B 5/7257; A61B 5/726; A61B 5/024; A61B 5/0536; A61B 5/242; A61B 5/339; A61B 5/341; A61B 5/369; A61B 5/7221; A61B 5/7278; A61B 2576/023; A61B 5/02028; A61B 5/026; A61B 5/0265; A61B 5/40; A61B 5/0044; A61B 5/1455; A61B 5/332; A61B 5/361; A61B 5/743; A61B 5/0022; A61B 5/7225; A61B 5/02; A61B 5/72; G16H 50/70; G16H 50/20; G16H 50/50; G16H 30/20; G16H 10/60; G16H 15/00; G16H 40/67; G16H 50/30; G06F 16/285; G06F 18/23; G06T 11/006; G06T 11/008; G06T 2200/08; G06T 2210/41; G06T 3/4007; G06T 11/60; G06T 17/20; G06T 2210/24; G06T 15/08; G06T 2207/10072; G06T 2207/30076; G06T 7/0012; G06T 7/13; G06N 3/045; G06N 3/08; G06N 20/00; G06N 3/02; G06N 3/126; G06N 7/01
See application file for complete search history.

(56) References Cited

U.S. PATENT DOCUMENTS

| | | | | |
|---|---|---|---|---|
| 2014/0194758 | A1* | 7/2014 | Korenberg | ........... A61B 5/7253 |
| | | | | 600/509 |
| 2015/0250450 | A1* | 9/2015 | Thomas | ................ A61B 8/085 |
| | | | | 600/407 |
| 2016/0378936 | A1 | 12/2016 | Burton | |
| 2019/0122397 | A1* | 4/2019 | Calhoun | .............. G06T 7/0012 |
| 2020/0202527 | A1 | 6/2020 | Chen | |
| 2020/0388037 | A1 | 12/2020 | Upton | |

OTHER PUBLICATIONS

Pages et al., "Generation of Computational Meshes From MRI and CT-SCAN Data", 2005, EDP Sciences, 213-223 (Year: 2005).*
Non-Final Office Action in U.S. Appl. No. 16/725,402 dated Nov. 21, 2024.
Chen, "A Chaotic Theoretical Approach to ECG-Based Identity Recognition" (Jan. 14, 2014).

* cited by examiner

Phase Energy Signal Data Visualization and Analysis

Phase Energy Signal Data Visualization and Analysis

CAD POSTIVE

Subendocardial ischemia necessary to induce regional
mechanical dissynergy.

Phase Energy Signal Data Visualization and Analysis

NORMAL
(NOT CAD POSITIVE)

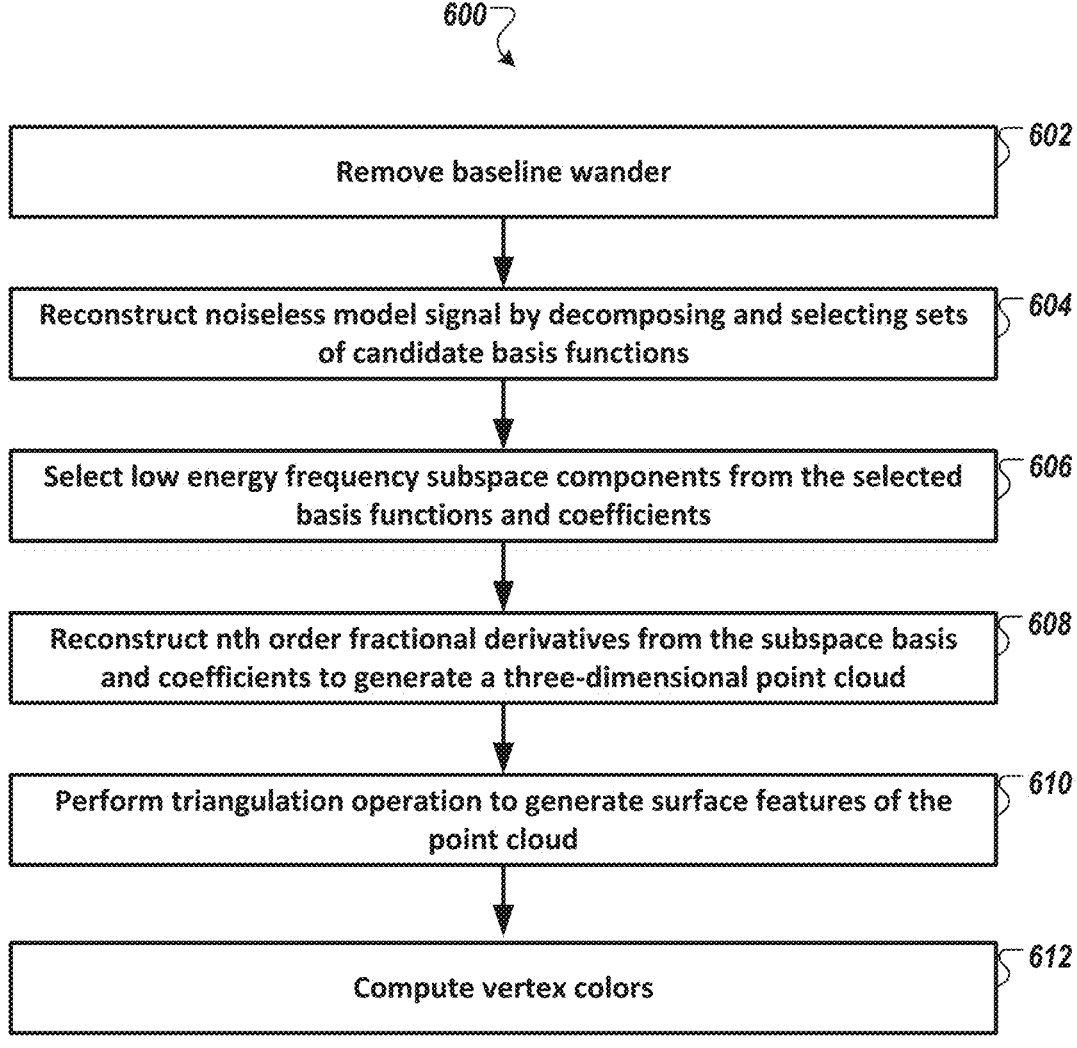

*600*

Remove baseline wander — *602*

Reconstruct noiseless model signal by decomposing and selecting sets of candidate basis functions — *604*

Select low energy frequency subspace components from the selected basis functions and coefficients — *606*

Reconstruct nth order fractional derivatives from the subspace basis and coefficients to generate a three-dimensional point cloud — *608*

Perform triangulation operation to generate surface features of the point cloud — *610*

Compute vertex colors — *612*

*FIG. 6*

| Characteristics | Development (n=235) | Test (n=50) | P-value |
|---|---|---|---|
| Mean Age – Years (Range) | 60.5 ± 28.5 | 57.8 ± 24.2 | 0.1005 |
| Male (%) | 69.8% | 66.0% | NS |
| Female (%) | 30.2% | 34.0% | NS |
| Mean BMI (Range) | 31.6 ± 26.4 | 33.4 ± 18.6 | NS |
| Diabetes Mellitus (%) | 37.0% | 32.0% | NS |
| Hypertension (%) | 74.0% | 80.0% | NS |
| Hypercholesterolemia/Hyperlipidemia (%) | 68.9% | 74.0% | NS |
| CAD Negative (%) | 68.1% | 70.0% | NS |
| CAD Positive (%) | 31.9% | 30.0% | NS |

*FIG. 31*

COR❤ISTA™                                    Ian Shadforth
                                             Piedmont Heart

| Patient | John Doe |
| Birthday | Jun 3, 1948 |
| Medical Record Number | 663277264 |
| Recording ID | 2471 |
| Time Acquired | 2016-12-30, 13:00:31 |

Phase space tomography

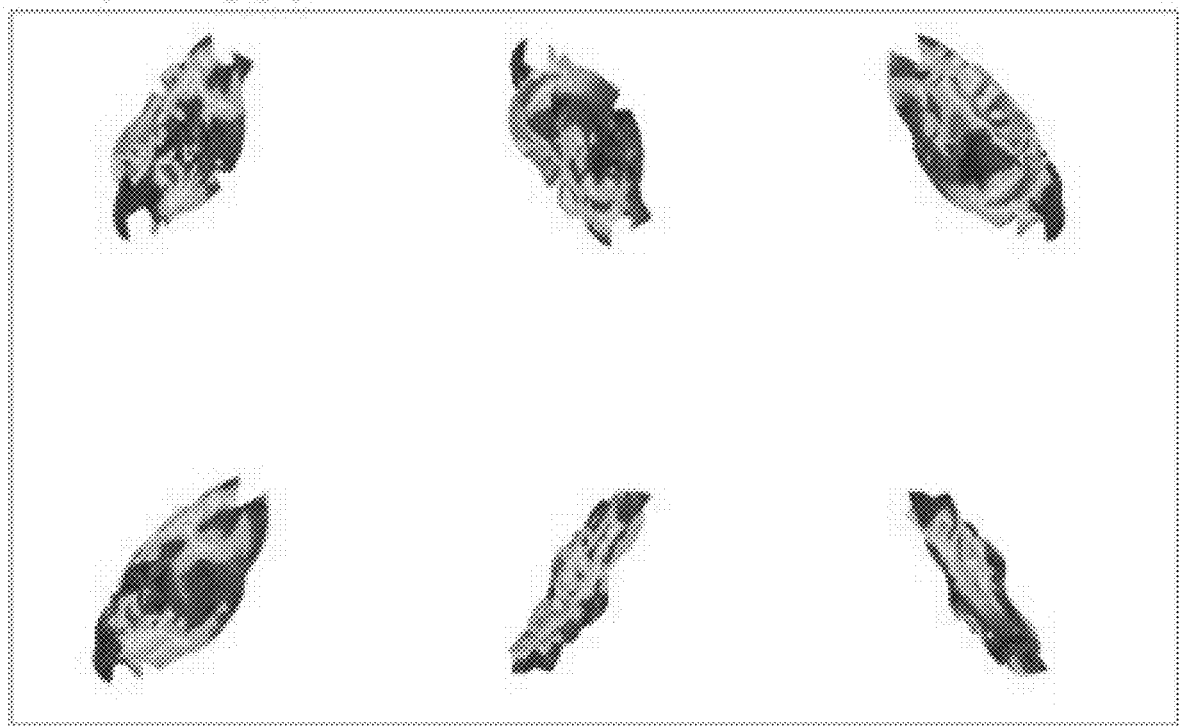

Predicted ischemic burden = 34

A predicted ischemic burden of > 8 has the following characteristics for the indication of significant CAD:
Sensitivity = 92%
Specificity = 62%
PPV = 47%
NPV = 96%
as demonstrated through the CADLAD Study

FIG. 36

METHOD AND SYSTEM TO ASSESS DISEASE USING PHASE SPACE TOMOGRAPHY AND MACHINE LEARNING

RELATED APPLICATIONS

This application claims priority to, and the benefit of, U.S. patent application Ser. No. 16/232,586, filed Dec. 26, 2018, titled "Method and System to Assess Disease Using Phase Space Tomography and Machine Learning", which claims priority to, and the benefit of, U.S. Provisional Appl. No. 62,612,130, filed Dec. 29, 2017, titled "Method and System to Assess Disease Using Phase Space Tomography and Machine Learning." Both applications are incorporated by reference herein in their entireties.

FIELD OF THE INVENTION

The present disclosure generally relates to non-invasive methods and systems for characterizing cardiovascular circulation and other physiological systems. More specifically, in an aspect, the present disclosure relates to non-invasive methods that utilize phase space data to generate a phase space tomographic images from an acquired biophysical signal (e.g., a cardiac signal, a brain/neurological signal, signals associated with other biological systems, etc.), in particular, to be used in the prediction and localization of coronary artery stenosis of the myocardium and characterize myocardial ischemia, among other cardiac and non-cardiac disease and pathologies.

BACKGROUND

Ischemic heart disease, or myocardial ischemia, is a disease or group of diseases characterized by reduced blood supply of the heart muscle, usually due to coronary artery disease (CAD). CAD typically can occur when the lining inside the coronary arteries that supply blood to the myocardium, or heart muscle, develops atherosclerosis (the hardening or stiffening of the lining and the accumulation of plaque therein, often accompanied by abnormal inflammation). Over time, CAD can also weaken the heart muscle and contribute to, e.g., angina, myocardial infarction (cardiac arrest), heart failure, and arrhythmias. An arrhythmia is an abnormal heart rhythm and can include any change from the normal sequence of electrical conduction of the heart and in some cases can lead to cardiac arrest.

The evaluation of CAD can be complex, and many techniques and tools are used to assess the presence and severity of the condition. In the case of electrocardiography, a field of cardiology in which the heart's electrical activity is analyzed to obtain information about its structure and function, significant ischemic heart disease can alter ventricular conduction properties of the myocardium in the perfusion bed downstream of the coronary artery narrowing or occlusion. This pathology can express itself at different locations of the heart and at different stages of severity, making an accurate diagnosis challenging. Further, the electrical conduction characteristics of the myocardium may vary from person to person, and other factors such as measurement variability associated with the placement of measurement probes and parasitic losses associated with such probes and their related components can also affect the biophysical signals that are captured during electrophysiologic tests of the heart. Further still, when conduction properties of the myocardium are captured as relatively long cardiac phase gradient signals, they may exhibit complex nonlinear variability that cannot be efficiently captured by traditional modeling techniques.

There is a benefit to having additional tools to non-invasively evaluate coronary artery disease and other cardiac disease, neurological disease, and other disease of other physiological systems.

SUMMARY

The exemplified intrinsic phase space tomography methods and systems facilitate the analysis and evaluation of complex, quasi-periodic system by generating tomographic images as a representation of the dynamics of the quasi-periodic cardiac systems. Indeed electrical conduction patterns of the heart, or other acquired biophysical signals of other organs, can be represented as phase space tomographic images generated as views of a phase space volumetric object (also referred to as a phase space model) that has both a volumetric structure (e.g., a three dimensional structure) and/or a color map. In some embodiments, the phase space tomographic images are presented as two-dimensional views of the phase space volumetric object to assist a physician in the assessment of presence or non-presence of disease. In other embodiments, the phase space tomographic image is presented as a three-dimensional representation of the phase space volumetric object. In some embodiments, the phase space tomographic images are used as input to a trained neural network classifier configured to assess for presence or non-presence of significant coronary artery disease. The phase space tomographic images and outputs of the classifier can be presented to a physician to assist in the assessment of presence or non-presence of disease. The exemplified methods and systems represents a new and efficient technique of assessing the presence of obstructive coronary lesions among other disease and pathologies.

In some embodiments, the methods and systems involve generating a noiseless subspace representation of a signal in three dimensions. Noiseless subspaces allow the observation of phase information of orthogonal leads that carries information about the structure of the heart and generates geometrical contrast in an image. This geometric contrast is caused by different bioelectric structures having different impedances, and so spectral and non-spectral conduction delays bend the trajectory of phase space orbit through the heart by different amounts. These small changes in trajectory can be normalized and quantified beat to beat and are represented in our model by the 20% lowest energy frequency subspace. Normalized phase space differentials of the low energy subspace are mapped to form the vertices of a geometric mesh for visualization. The mesh is then colored by the difference between the model and the original signal. The result is the three-dimensional phase space volumetric object which can be evaluated via a trained neural network classifier to produce the phase space tomographic image.

In some embodiments, contours and heat map of the tomographic images or of the assessed classifiers are generated and presented, separately or overlaid over the tomographic images or over the assessed classifier, to aid a physician in the evaluation of the acquired data. The tomographic images can be evaluated by physician alongside with results of a machine-generated formula to allow the physician an opportunity to make a more informed judgement of the results.

In some embodiments, the features of the volumetric structure and/or a color map of the phase space tomographic images are extracted and evaluated to assess for the presence and/or absence of pathologies, e.g., ischemia relating to significant coronary arterial disease (CAD). In some embodiments, the phase space volumetric object can be assessed to extract topographic and geometric parameters, e.g., in a tomographic analysis, that are used in models that determine indications of presence or non-presence of significant coronary artery disease.

As used herein, the term "cardiac signal" refers to one or more signals associated with the structure, function and/or activity of the cardiovascular system—including aspects of that signal's electrical/electrochemical conduction—that, e.g., cause contraction of the myocardium. A cardiac signal may include, in some embodiments, electrocardiographic signals such as, e.g., those acquired via an electrocardiogram (ECG) or other modalities.

As used herein, the term "neurological signal" refers to one or more signals associated with the structure, function and/or activity of the central and peripheral nervous systems, including the brain, spinal cord, nerves, and their associated neurons and other structures, etc., and including aspects of that signal's electrical/electrochemical conduction. A neurological signal may include, in some embodiments, electroencephalographic signals such as, e.g., those acquired via an electroencephalogram (EEG) or other modalities.

As used herein, the term "biophysical signal" is not meant to be limited to a cardiac signal and/or a neurological signal but encompasses any physiological signal from which information may be obtained. Not intending to be limited by example, one may classify biophysical signals into types or categories that can include, for example, electrical (e.g., certain cardiac and neurological system-related signals that can be observed, identified and/or quantified by techniques such as the measurement of voltage/potential, impedance, resistivity, conductivity, current, etc. in various domains such as time and/or frequency), magnetic, electromagnetic, optical (e.g. signals that can be observed, identified and/or quantified by techniques such as reflectance, interferometry, spectroscopy, absorbance, transmissivity, visual observation and the like), acoustic, chemical, mechanical (e.g., signals related to fluid flow, pressure, motion, vibration, displacement, strain), thermal, and electrochemical (e.g. signals that can be correlated to the presence of certain analytes, such as glucose). Biophysical signals may in some cases be described in the context of a physiological system (e.g., respiratory, circulatory (cardiovascular, pulmonary), nervous, lymphatic, endocrine, digestive, excretory, muscular, skeletal, renal/urinary/excretory, immune, integumentary/exocrine and reproductive systems), an organ system (e.g., signals that may be unique to the heart and lungs as they work together), or in the context of tissue (e.g., muscle, fat, nerves, connective tissue, bone), cells, organelles, molecules (e.g., water, proteins, fats, carbohydrates, gases, free radicals, inorganic ions, minerals, acids, and other compounds, elements and their subatomic components. Unless stated otherwise, the term "biophysical signal acquisition" generally refers to any passive or active means of acquiring a biophysical signal from a physiological system, such as a mammalian or non-mammalian organism. Passive biophysical signal acquisition generally refers to the observation of natural electrical, magnetic, and/or acoustics emittance of the body tissue. Non-limiting examples of passive biophysical signal acquisition means includes, e.g., voltage/potential, current, magnetic, acoustic, optical, and other non-active ways of observing the natural emittance of the body tissue. Non-limiting examples of active biophysical signal acquisition means include, e.g., ultrasound, radio waves, microwaves, infrared and/or visible light (e.g., for use in pulse oximetry), visible light, ultraviolet light and other ways of actively interrogating the body tissue that does not involve ionizing energy or radiation (e.g., X-ray). Active biophysical signal acquisition means that involves ionizing energy or radiation (e.g., X-ray) are referred to as "ionizing biophysical signal", which can be acquired invasively (e.g., via surgery or invasive radiologic intervention protocols) or non-invasively (e.g., via imaging).

In an aspect, a method is disclosed for non-invasively assessing presence or non-presence of significant coronary artery disease. The method includes obtaining, by one or more processors (e.g., from a stored database or from a measurement equipment), acquired data from a measurement of one more biophysical signals of a subject (e.g., biopotential-based signals, ultrasound-based signals, magnetic-based signals), wherein the acquired data is derived from measurements acquired via noninvasive equipment configured to measure properties (e.g., electric properties, magnetic properties, acoustic properties, impedance properties, and etc.) of the heart; and generating, by the one or more processors, a set of tomographic images derived from a phase space model generated based on the acquired data, wherein at least one of the phase space model comprises a plurality of faces and a plurality of vertices, wherein the plurality of vertices are defined, in part, by a fractional subspace derivative operation and by low-energy subspace parameters generated directly or indirectly from the acquired data (e.g., wherein the position values of the vertices are based on low-energy subspace parameters determined from a model-derived reconstruction operation); wherein the set of tomographic images are presented (e.g., on a local or a remote computing system) for the assessment of presence and/or non-presence of significant coronary artery disease.

In some embodiments, the method includes determining, by the one or more processors, a machine-trained assessment of presence and/or non-presence of significant coronary artery disease using a trained neural network-based nonlinear classifier configured to map individual pixels of the tomographic images to a binary predictor.

In some embodiments, the method includes generating a contour data set for each tomographic image of the set of tomographic images, wherein the contour data are presented for the assessment of presence and/or non-presence of significant coronary artery disease.

In some embodiments, the contour data set is generated by sweeping, via the one or more processors, a moving window associated with the trained neural network-based nonlinear classifier on a pixel by pixel basis over, at least a portion of, a given tomographic image; and combining, for a given pixel of the tomographic image, outputs of the swept moving window.

In some embodiments, the method includes presenting, via a display of a remote computing system, the generated contour data set.

In some embodiments, the method includes presenting, via the display of the remote computing system, the generated contour data set and a corresponding tomographic image used to generate the contour data set, wherein the generated contour data set is rendered as an overlay over the corresponding tomographic image.

In some embodiments, the generated contour data set comprises color map data.

In some embodiments, the method includes presenting, via a display of the remote computing system, the set of tomographic images in conjunction with the generating a contour data set.

In some embodiments, the vertices and faces of the generated phase space model comprises color data, the steps of generating the tomographic images comprising converting the generated phase space model to greyscale.

In some embodiments, the tomographic images are generated by generating a plurality of images corresponding to a plurality of orientation of the generated phase space model, wherein the image are generated at a first image resolution; and converting the plurality of images to a second image resolution, wherein the second image resolution is different from the first image resolution (e.g., wherein the second image resolution has a lower number of pixels as compared to the first image resolution).

In another aspect, a method is disclosed for non-invasively measuring myocardial ischemia (determining presence thereof; determining location(s) thereof and/or areas impacted by condition; and/or determining a degree thereof), measuring one or more stenoses (e.g., determining presence thereof; and/or determining localization thereof; and/or determining a degree thereof), or measuring fractional flow reserve (e.g., estimating value thereof at an identified stenosis). The method includes obtaining, by one or more processors, acquired data from a measurement of one more electrical signals of a subject (e.g., biopotential-based signals, ultrasound-based signals, magnetic-based signals), wherein the acquired data is derived from measurements acquired via noninvasive equipment configured to measure properties (e.g., electric properties, magnetic properties, acoustic properties, impedance properties, and etc.) of the heart; generating, by the one or more processors, one or more phase space models (e.g., phase space volumetric objects) based on the acquired data, wherein at least one of the one or more phase space models comprises a plurality of faces and a plurality of vertices, wherein the plurality of vertices are defined, in part, by fractional subspace derivative operations of low-energy subspace parameters generated directly or indirectly from the acquired data; and determining, by the one or more processors, one or more coronary physiological parameters of the subject selected from the group consisting of a fractional flow reserve estimation, a stenosis value, and a myocardial ischemia estimation, based on the generated phase space volumetric object (e.g., and causing, by the one or more processors, output of the one or more coronary physiological parameters (e.g., in a report, a display, instrumentation output, etc.)).

In some embodiments, the generated phase space volumetric object comprises a three-dimensional object defined by the plurality of faces and a plurality of vertices.

In some embodiments, the plurality of vertices are generated as a point cloud in 3D space (e.g., having X, Y, and Z components), wherein each point in the point cloud has a value (e.g., color value) associated with a fractional order of a fractional subspace derivative operation of the low-energy subspace parameters (e.g., wherein a fractional subspace derivative operation of the low-energy subspace parameters for a given fractional order generates a 2D data set).

In some embodiments, each fractional order of the fractional subspace derivative operation is predetermined and corresponds to a frequency, or a range thereof, of electrical conduction events of the heart including those associated with activation (e.g., ventricular and/or atrio depolarization) of the various chambers and recovery (i.e., ventricular and/or atrio repolarization).

In some embodiments, each of the plurality of vertices or each of the plurality of faces comprises one or more attribute parameters (e.g., color).

In some embodiments, each of the plurality of vertices or each of the plurality of faces comprises one or more color attribute parameters.

In some embodiments, at least one of the one or more color attribute parameters is associated with a variance of a modeled channel signal generated from a model-derived construction (e.g., a sparse approximation algorithm such as, or based on, principal component analysis (PCA), matching pursuit, orthogonal matching pursuit, orthogonal search, projection pursuit, LASSO, fast orthogonal search, Sparse Karhunen-Loeve Transform, and combinations thereof) of the acquired data subtracted from a baseline-removed raw channel of the acquired data.

In some embodiments, the plurality of faces are generated from a triangulation operation of the plurality of vertices.

In some embodiments, the plurality of faces are generated from the triangulation operation, the triangulation operation being selected from the group consisting of Delaunay triangulation, Mesh generation, Alpha Hull triangulation, and Convex Hull triangulation.

In some embodiments, each of the plurality of faces comprises one or more face attribute parameters (e.g., color).

In some embodiments, each of the plurality of faces comprises one or more face color attribute parameters.

In some embodiments, at least one of the one or more face color attribute parameters is a triangular interpolation among bounding vertex attribute parameters (e.g., 3 bound vertex colors).

In some embodiments, the fractional order is a rational number or an irrational number associated with one or more linear and/or non-linear dynamic response of the heart.

In some embodiments, the method further includes removing, by the one or more processors, a baseline wandering trend from the acquired data prior to generating the one or more phase space models.

In some embodiments, the method further includes performing a model-derive reconstruction operation of the acquired data to generate the low-energy subspace parameters, the low-energy subspace parameters comprising a plurality of basis functions and coefficients (e.g., a linear combination of plurality of basis functions scaled by one or more coefficients).

In some embodiments, the low-energy subspace parameters consist of low-energy subsets of plurality of basis functions and coefficients.

In some embodiments, the low-energy subsets of plurality of basis functions and coefficients are selected from the group consisting of: about 1% of plurality of basis functions and coefficients associated with low energy frequency subspace; about 5% of plurality of basis functions and coefficients associated with low energy frequency subspace; about 10% of plurality of basis functions and coefficients associated with low energy frequency subspace; about 15% of plurality of basis functions and coefficients associated with low energy frequency subspace; about 20% of plurality of basis functions and coefficients associated with low energy frequency subspace; and about 25% of plurality of basis functions and coefficients associated with low energy frequency subspace.

In some embodiments, the model-derived reconstruction operation generates over 100 basis functions and coefficients for a given acquired data.

In some embodiments, parameters associated with generated one or more phase space models are used in subsequent machine learning operations (e.g., image-based machine learning operations or feature-based machine learning operations) to determine the one or more coronary physiological parameters.

In some embodiments, the parameters associated with generated one or more phase space models are associated with geometric properties of the generated one or more phase space models.

In some embodiments, the parameters associated with generated one or more phase space models are associated with geometric properties of the generated one or more phase space models selected from the group consisting of volume, number of distinct bodies, and color gradient.

In some embodiments, the method further includes causing, by the one or more processors, generation of a visualization of generated phase space volumetric model as a three-dimensional object, wherein the three-dimensional object is rendered and displayed at a display of a computing device (e.g., computing workstation; a surgical, diagnostic, or instrumentation equipment).

In some embodiments, the method further includes causing, by the one or more processors, generation of a visualization of generated phase space volumetric model as a three-dimensional object, wherein the three-dimensional object is displayed in a report (e.g., an electronic report).

In some embodiments, the acquired data comprises differential channel signals (e.g., 3 sets of differential measurement simultaneously sampled; or 6 sets of unipolar measurements simultaneously sampled).

In some embodiments, the acquired data comprise signals associated with interference (e.g., in phase plane) of depolarization waves among orthogonal leads.

In some embodiments, the method further includes extracting a first set of morphologic features of the generated phase space volumetric model, wherein the first set of extracted morphologic features include parameters selected from the group consisting of a 3D volume value, a void volume value, a surface area value, a principal curvature direction value, and a Betti number value.

In some embodiments, the method further includes dividing the generated phase space volumetric model into a plurality of segments each comprising non-overlapping portions of the generated phase space volumetric model; and extracting a set of morphologic features of each of the plurality of segments, wherein the second set of extracted morphologic features includes parameters selected from the group consisting of a 3D volume value, a void volume value, a surface area value, a principal curvature direction value, and a Betti number value.

In some embodiments, the plurality of segments comprise a number of segments selected from the group consisting of 3, 4, 5, 6, 7, 8, 9, 10, 11, 12, 13, 14, 15, 16, 17, 18, 19, and 20.

In some embodiments, the acquired data are acquired as one or more wide-band gradient signals simultaneously from the subject via at least one electrode.

In some embodiments, at least one of one or more wide-band gradient signals comprise a high-frequency time series data that is unfiltered (e.g., spectrally unmodified) prior to the processing in the phase-space analysis.

In some embodiments, the one or more wide-band gradient signals comprise cardiac frequency information at a frequency selected from the group consisting of about 1 kHz, about 2 kHz, about 3 kHz, about 4 kHz, about 5 kHz, about 6 kHz, about 7 kHz, about 8 kHz, about 9 kHz, about 10 kHz, and greater than 10 kHz (e.g., 0-50 kHz or 0-500 kHz).

In another aspect, a system is disclosed comprising a processor; and a memory having instructions thereon, wherein the instructions when executed by the processor, cause the processor to perform any of the above method.

In another aspect, a non-transitory computer readable medium is disclosed having instructions stored thereon, wherein execution of the instructions, cause the processor to perform any of the above method.

BRIEF DESCRIPTION OF THE DRAWINGS

The accompanying drawings, which are incorporated in and constitute a part of this specification, illustrate embodiments and together with the description, serve to explain the principles of the methods and systems.

Embodiments of the present invention may be better understood from the following detailed description when read in conjunction with the accompanying drawings. Such embodiments, which are for illustrative purposes only, depict novel and non-obvious aspects of the invention. The drawings include the following figures:

FIG. 6 is an example method of generating a phase space volumetric object by the non-invasive cardiac assessment system in accordance with an illustrative embodiment.

FIG. 31 shows a table with characteristics of a development and test data set used to train a neural network classifier in accordance with an illustrative embodiment.

FIGS. 32, 33, 34, 35, 36, 37, 38, and 39 show example graphical user interface for a clinician web portal, or a report derived therefrom, to view and assess cardiac phase space tomographic images, in accordance with an illustrative embodiment.

DETAILED SPECIFICATION

Each and every feature described herein, and each and every combination of two or more of such features, is included within the scope of the present invention provided that the features included in such a combination are not mutually inconsistent.

While the present disclosure is directed to the beneficial assessment of biophysical signals in the diagnosis and treatment of cardiac-related pathologies and conditions and/or neurological-related pathologies and conditions, such assessment can be applied to the diagnosis and treatment (including, surgical, minimally invasive, and/or pharmacologic treatment) of any pathologies or conditions in which a biophysical signal is involved in any relevant system of a living body. One example in the cardiac context is the diagnosis of CAD and its treatment by any number of therapies, alone or in combination, such as the placement of a stent in a coronary artery, performance of an atherectomy, angioplasty, prescription of drug therapy, and/or the prescription of exercise, nutritional and other lifestyle changes, etc. Other cardiac-related pathologies or conditions that may be diagnosed include, e.g., arrhythmia, congestive heart failure, valve failure, pulmonary hypertension (e.g., pulmonary arterial hypertension, pulmonary hypertension due to left heart disease, pulmonary hypertension due to lung disease, pulmonary hypertension due to chronic blood clots, and pulmonary hypertension due to other disease such as blood or other disorders), as well as other cardiac-related pathologies, conditions and/or diseases. Non-limiting examples of neurological-related diseases, pathologies or conditions that may be diagnosed include, e.g., epilepsy, schizophrenia, Parkinson's Disease, Alzheimer's Disease (and all other forms of dementia), autism spectrum (including Asperger syndrome), attention deficit hyperactivity disorder, Huntington's Disease, muscular dystrophy, depression, bipolar disorder, brain/spinal cord tumors (malignant and benign), movement disorders, cognitive impairment, speech impairment, various psychoses, brain/spinal cord/nerve injury, chronic traumatic encephalopathy, cluster headaches, migraine headaches, neuropathy (in its various forms, including peripheral neuropathy), phantom limb/pain, chronic fatigue syndrome, acute and/or chronic pain (including back pain, failed back surgery syndrome, etc.), dyskinesia, anxiety disorders, conditions caused by infections or foreign agents (e.g., Lyme disease, encephalitis, rabies), narcolepsy and other sleep disorders, post-traumatic stress disorder, neurological conditions/effects related to stroke, aneurysms, hemorrhagic injury, etc., tinnitus and other hearing-related diseases/conditions and vision-related diseases/conditions.

Example System

Figure 1:
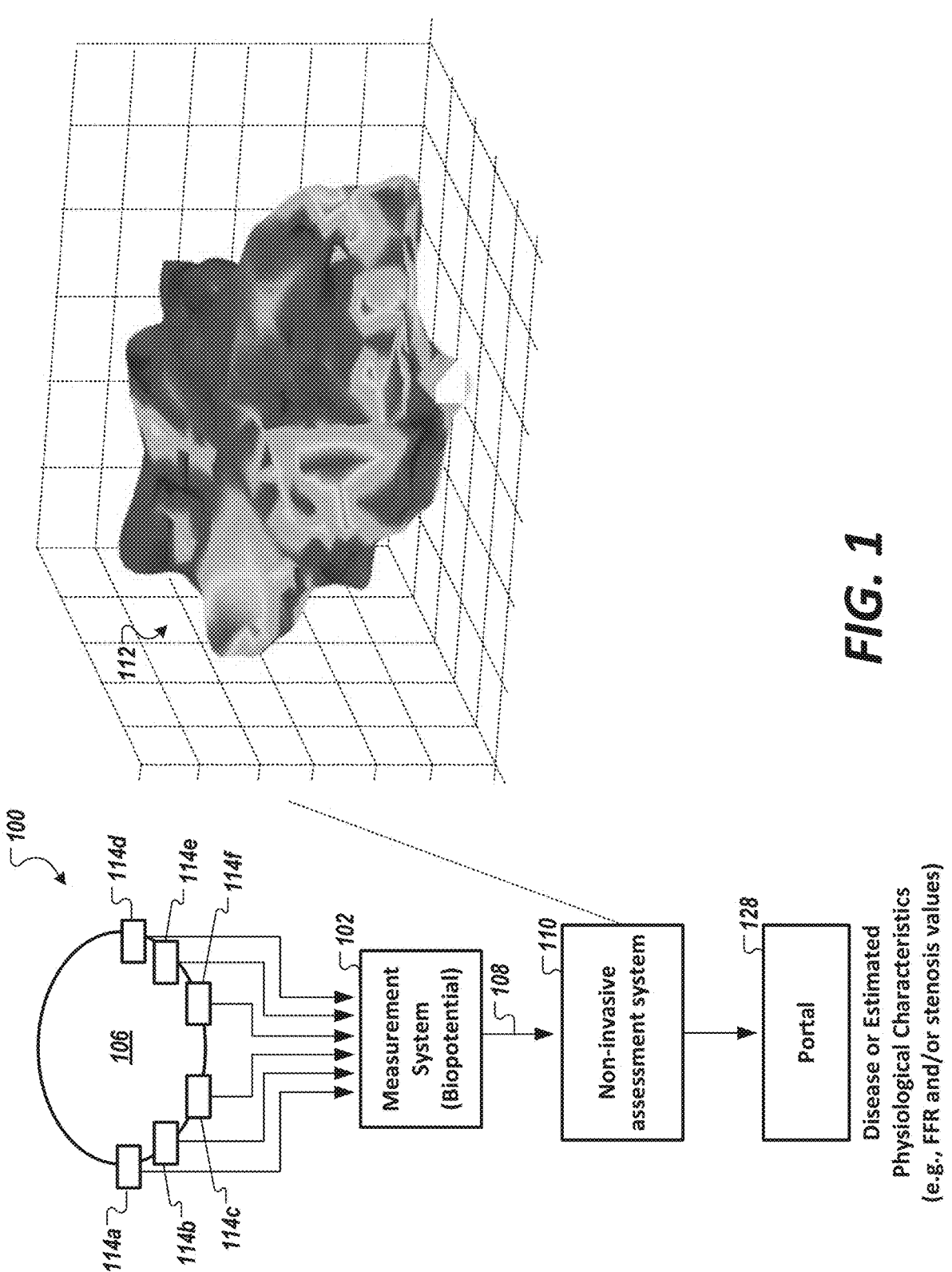
FIG. 1 is a diagram of an example system configured to assess non-invasively presence or non-presence of a disease state (e.g., significant coronary artery disease) using biophysical phase gradient computed tomography (also referred to herein as computed phase space tomography), in accordance with an illustrative embodiment.

FIG. 1 is a diagram of an example system 100 configured to assess (e.g., non-invasively assess) presence or non-presence of a disease state (e.g., significant coronary artery disease) in a physiological system of a subject using cardiac phase gradient computed tomography (also referred to as computed phase space tomography), in accordance with an illustrative embodiment. As noted herein, physiological systems can refer to the cardiovascular system, the pulmonary system, the renal system, the nervous system, and other functional systems and sub-systems of the body. In the context of the cardiovascular system, the particular embodiment of the system 100 facilitates the investigation of complex, nonlinear systems of the heart by examining in phase space the states, or phases, that such a system may exhibit over many cycles.

In FIG. 1, measurement system 102 is a non-invasive embodiment (shown as "Measurement System (biophysical)" 102) that acquires a plurality of biophysical signals 104 (e.g., phase gradient biophysical signals) via measurement probes 114 (shown as probes 114a, 114b, 114c, 114d, 114c, and 114f) from a subject 106 to produce a phase-gradient biophysical data set 108. Assessment system 110 (shown as "Non-invasive assessment system" 110) receives the phase-gradient biophysical data set 108 and generates one or more phase space volumetric objects 112 (also referred to herein as a "phase space volumetric model" 112) for analysis of the phase-gradient biophysical data set 108. Each of the phase space volumetric objects 112 as a three-dimensional structure includes a plurality of vertices generated as a point cloud in three-dimensional space and a plurality of faces defined by the plurality of vertices. The assessment system 110 can further determine, in some embodiments, a set of computed phase space tomographic images from the phase space volumetric objects 112. A machine learned classifier can be applied on the computed phase space tomographic images or the computed phase gradient tomographic images from which the images are derived to assess the contextual information on cardiac health. The color and shape of the phase space volumetric objects 112 and computed phase space tomographic images derived therefrom beneficially synthesize and display the electrical and functional characteristics of the heart.

In FIG. 1, system 100, in some embodiments, includes a healthcare provider portal (shown as "Portal" 128) configured to display stored phase space volumetric objects 112 or images derived therefrom (among other intermediate data sets) in a phase space tomographic and/or angiographic-equivalent report. Portal 128, which in some embodiments may be termed a physician or clinician portal 128, is configured to access, retrieve, and/or display or present reports and/or the phase space tomographic volumetric images (and other data) for the report from a repository (e.g., a storage area network).

In some embodiments, and as shown in FIG. 1, the healthcare provider portal 128 is configured to display phase space volumetric objects 112 or images derived therefrom in, or along with, an anatomical mapping report, a coronary tree report, and/or a 17-segment report. Portal 128 may present depictions of rotatable and optionally scalable three-dimensional phase space volumetric objects 112 or images derived therefrom. Portal 128 may present the data, e.g., in real-time (e.g., as a web object), as an electronic document, and/or in other standardized or non-standardized image visualization/medical data visualization/scientific data visualization formats. The anatomical mapping report, in some embodiments, includes one or more depictions of a rotatable and optionally scalable three-dimensional anatomical map of cardiac regions of affected myocardium. The anatomical mapping report, in some embodiments, is configured to display and switch between a set of one or more three-dimensional views and/or a set of two-dimensional views of a model having identified regions of myocardium. The coronary tree report, in some embodiments, includes one or more two-dimensional view of the major coronary artery. The 17-segment report, in some embodiments, includes one or more two-dimensional 17-segment views of corresponding regions of myocardium. In each of the report, the value that indicates presence of cardiac disease or condition at a location in the myocardium, as well as a label indicating presence of cardiac disease, may be rendered as both static and dynamic visualization elements that indicates area of predicted blockage, for example, with color highlights of a region of affected myocardium and with an animation sequence that highlight region of affected coronary arter(ies). In some embodiments, each of the report includes textual label to indicate presence or non-presence of cardiac disease (e.g., presence of significant coronary artery disease) as well as a textual label to indicate presence (i.e., location) of the cardiac disease in a given coronary artery disease.

In some embodiments, the Portal 128 is configured to display phase space volumetric objects 112 and/or stored phase space tomographic volumetric images (among other intermediate data sets) in the phase space tomographic and/or angiographic-equivalent report. The physician or clinician portal 128, in some embodiments, is configured to access and retrieve reports or the phase space tomographic volumetric images (and other data) for the report) from a repository (e.g., a storage area network). The physician or clinician portal 128 and/or repository can be compliant with patient information and other personal data privacy laws and regulations (such as, e.g., the U.S. Health Insurance Portability and Accountability Act of 1996 and the EU General Data Protection Regulation) and laws relating to the marketing of medical devices (such as, e.g., the US Federal Food and Drug Act and the EU Medical Device Regulation). Further description of an example healthcare provider portal 128 is provided in U.S. Publication No. 2018/0078146, title "Method and System for Visualization of Heart Tissue at Risk", which is incorporated by reference herein in its entirety. Although in certain embodiments, Portal 128 is configured for presentation of patient medical information to healthcare professionals, in other embodiments, the healthcare provider portal 128 can be made accessible to patients, researchers, academics, and/or other portal users.

In the context of cardiovascular systems, in some embodiments, the healthcare provider portal (and corresponding user interface) 128 is configured to present summary information visualizations of myocardial tissue that identifies myocardium at risk and/or coronary arteries that are blocked. The user interface can be a graphical user interface ("GUI") with a touch- or pre-touch sensitive screen with input capability. The user interface can be used, for example, to direct diagnostics and treatment of a patient and/or to assess patients in a study. The visualizations, for a given report of a study, may include multiple depictions of a rotatable three-dimensional anatomical map of cardiac regions of affected myocardium, a corresponding two-dimensional view of the major coronary arteries, and a corresponding two-dimensional 17-segment view of the major coronary arteries to facilitate interpretation and assessment of architectural features of the myocardium for characterizing abnormalities in the heart and in cardiovascular functions.

The measurement system 102, in some embodiments, is configured to acquire biophysical signals that may be based on the body's biopotential via biopotential sensing circuitries as biopotential biophysical signals. In the cardiac and/or electrocardiography contexts, measurement system 102 is configured to capture cardiac-related biopotential or electrophysiological signals of a living organism (such as a human) as a biopotential cardiac signal data set. In some embodiments, measurement system 102 is configured to acquire a wide-band cardiac phase gradient signals as a biopotential signal or other signal types (e.g., a current signal, an impedance signal, a magnetic signal, an optical signal, an ultrasound or acoustic signal, etc.). The term "wide-band" in reference to an acquired signal, and its corresponding data set, refers to the signal having a frequency range that is substantially greater than the Nyquist sampling rate of the highest dominant frequency of a physiological system of interest. For cardiac signals, which typically have dominant frequency components between about 0.5 Hz and about 80 Hz, the wide-band cardiac phase gradient signals or wide-band cardiac biophysical signals comprise cardiac frequency information at a frequency selected from the group consisting between about 0.1 Hz and about 1 KHz, between about 0.1 Hz and about 2 KHz, between about 0.1 Hz and about 3 KHz, between about 0.1 Hz and about 4 KHz, between about 0.1 Hz and about 5 KHz, between about 0.1 Hz and about 6 KHz, between about 0.1 Hz and about 7 KHz, between about 0.1 Hz and about 8 KHz, between about 0.1 Hz and about 9 KHz, between about 0.1 Hz and about 10 KHz, and between about 0.1 Hz and greater than 10 KHz (e.g., 0.1 Hz to 50 KHz or 0.1 Hz to 500 KHz). In addition to capturing the dominant frequency components, the wide-band acquisition also facilitate capture of other frequencies of interest. Examples of such frequencies of interest can include QRS frequency profiles (which can have frequency ranges up to about 250 Hz), among others. The term "phase gradient" in reference to an acquired signal, and its corresponding data set, refers to the signal being acquired at different vantage points of the body to observe phase information for a set of distinct events/functions of the physiological system of interest. Following the signal acquisition, the term "phase gradient" refers to the preservation of phase information via use of non-distorting signal processing and pre-processing hardware, software, and techniques (e.g., phase-linear filters and signal-processing operators and/or algorithms).

In the neurological context, measurement system 102 is configured to capture neurological-related biopotential or electrophysiological signals of a living subject (such as a human) as a neurological biophysical signal data set. In some embodiments, measurement system 102 is configured to acquire wide-band neurological phase gradient signals as a biopotential signal or other signal types (e.g., a current signal, an impedance signal, a magnetic signal, an ultrasound, an optical signal, an ultrasound or acoustic signal, etc.). Examples of measurement system 102 are described in U.S. Publication No. 2017/0119272 and in U.S. Publication No. 2018/0249960, each of which is incorporated by reference herein in its entirety.

In some embodiments, measurement system 102 is configured to capture wide-band biopotential biophysical phase gradient signals as unfiltered electrophysiological signals such that the spectral component(s) of the signals are not altered. Indeed, in such embodiments, the wide-band biopotential biophysical phase gradient signals are captured, converted, and even analyzed without having been filtered (via, e.g., hardware circuitry and/or digital signal processing techniques, etc.) (e.g., prior to digitization) that otherwise can affect the phase linearity of the biophysical signal of interest. In some embodiments, the wide-band biopotential biophysical phase gradient signals are captured in microvolt or sub-microvolt resolutions that are at, or significantly below, the noise floor of conventional electrocardiographic, electroencephalographic, and other biophysical-signal acquisition instruments. In some embodiments, the wide-band biopotential biophysical signals are simultaneously sampled having a temporal skew or "lag" of less than about 1 microseconds, and in other embodiments, having a temporal skew or lag of not more than about 10 femtoseconds. Notably, the exemplified system minimizes non-linear distortions (e.g., those that can be introduced via certain filters) in the acquired wide-band phase gradient signal to not affect the information therein.

Referring still to FIG. 1, the plurality of vertices of the phase space volumetric object is spatially defined, in some embodiments, by the subspace data set (e.g., a low-energy frequency subspace data set) of a three dimensional phase space model generated from the phase-gradient biophysical data set 108. Further, each, or a substantial portion, of the plurality of vertices of the phase space volumetric object 112 has one or more values (e.g., a color value) that correspond to a fractional order derivative operation as applied, for example, to, the phase-gradient biophysical data set 108, and/or the three dimensional phase space model generated from the phase-gradient biophysical data set 108. The three dimensional phase space model can be configured as a set of time series data of three sets of differential channel signals derived from the phase-gradient biophysical data set 108. The fractional derivative operations can be used, for instance, to compensate for noise, lead placement errors and to create more accurate tissue impedance models.

The phase space volumetric objects 112 includes a plurality of faces generated by a triangulation operation on the three-dimensional point cloud. In some embodiments, the triangulation operation includes an Alpha Hull triangulation operation of the three-dimensional time-series points in which a predetermined radius α is used to generate faces that are mapped to the plurality of vertices. In other embodiments, Delaunay triangulation, alpha shapes, ball pivoting, Mesh generation, Convex Hull triangulation, and the like, is used.

As discussed in U.S. Publication No. 2013/0096394, which is incorporated by reference herein in its entirety, a mathematical reconstruction of the phase-gradient biophysical data signal may comprise various elements including, in some embodiments, an input/output (I/O) expansion of the phase-gradient biophysical data signal in which at least one of the terms of the I/O expansion are fractionally differentiable (e.g., analytically fractionally differentiable). In some embodiments, the I/O expansion comprises a fractional integral of the mathematical reconstruction. Sparse approximation operation comprises a set of operations, often iterative, to find a best matching projection of a data set (e.g., multi-dimensional data) onto candidate functions in a dictionary. Each dictionary can be a family of waveforms that is used to decompose the input data set. The candidate functions, in some embodiments, are linearly combined to form a sparse representation of the input data set. These operations can be numerical or analytical. In some embodiments, the mathematical reconstruction is based on principal component analysis (PCA), matching pursuit, orthogonal matching pursuit, orthogonal search, projection pursuit, LASSO, fast orthogonal search, Sparse Karhunen-Loeve Transform, or combinations thereof. In other embodiments, the I/O expansion comprises an irrational fractional subspace derivative of the mathematical reconstruction of the phase-gradient biophysical data signal. The recited examples are not exhaustive and other sparse approximation algorithms or methods may be used as well as any variations and combinations thereof.

As discussed in U.S. Publication No. 2013/0096394, there are a couple of points about the low-energy component subspace (made from the last, e.g., 20% terms found by a matching pursuit reconstruction algorithm operation) that are interesting and useful. First, the fractional integral and derivative of these components can be noiselessly determined, since it is a linear combination of selected candidate terms, and this fractional derivative can be useful to distinguish ventricular tachycardia potential in post myocardial infarction patients and those with congenital heart defects. In addition, there are some useful fractional properties to consider. Thus suppose that x(t), y(t), and z(t) are respectively the X, Y, and Z coordinates of the low-energy component and let $x_a(t)$, $y_a(t)$, and $z_a(t)$ be their irrational fractional derivative of order a that can be any real or complex number.

In some embodiments, the fractional derivative operation is based on Grünwald-Letnikov fractional derivative method. In some embodiments, the fractional derivative operation is based on the Lubich's fractional linear multi-step method. In some embodiments, the fractional derivative operation is based on the fractional Adams-Moulton method. In some embodiments, the fractional derivative operation is based on the Riemann-Liouville fractional derivative method. In some embodiments, the fractional derivative operation is based on Riesz fractional derivative method. Other methods of performing a fractional derivative may be used.

To predict presence or non-presence of significant coronary artery disease from the phase-space tomographic images, a trained neural network is applied, in some embodiments, to a number of views (e.g., six views) of each tomographic image (e.g., top, bottom, front, back, left and right view). In some embodiments, images acquired of the three-dimensional volumetric object 112 is first converted to grayscale and scaled to a pre-defined image resolution (e.g., 195×128 pixels). Other pixel count and image resolution can be used. In some embodiments, the neural network classifier includes multiple hidden neurons (e.g., 15 hidden neurons) with leaky rectified linear activations. Dropout may be used between the hidden layer and the final output neuron to prevent overfitting. L1 and L2 regularization penalties may also be applied. A binary cross entropy may be used as a loss function. Optimization may be performed using the gradient-based Adam algorithm.

Heat maps and contour plots, in some embodiments, are generated from the outputs of the neural network classifier on a given phase-space tomographic image or from the computed phase space tomographic images themselves. In some embodiments, a 4×4 moving window of white pixels (e.g., having a value of 1 in grayscale images) is swept over the entire image, with the neural network classifier being evaluated once for each window position and the output of the neural network being recorded. When a given pixel in the PST image is covered by the moving window more than once (e.g., when the window is larger than a single pixel but moving one pixel at a time), each pixel in the heat map may have a value that is an average output of the neural network classifier when the corresponding pixel in the phase-space tomographic image is covered by the window. Contour plots may be generated using the same data as the heat maps.

Figure 2:
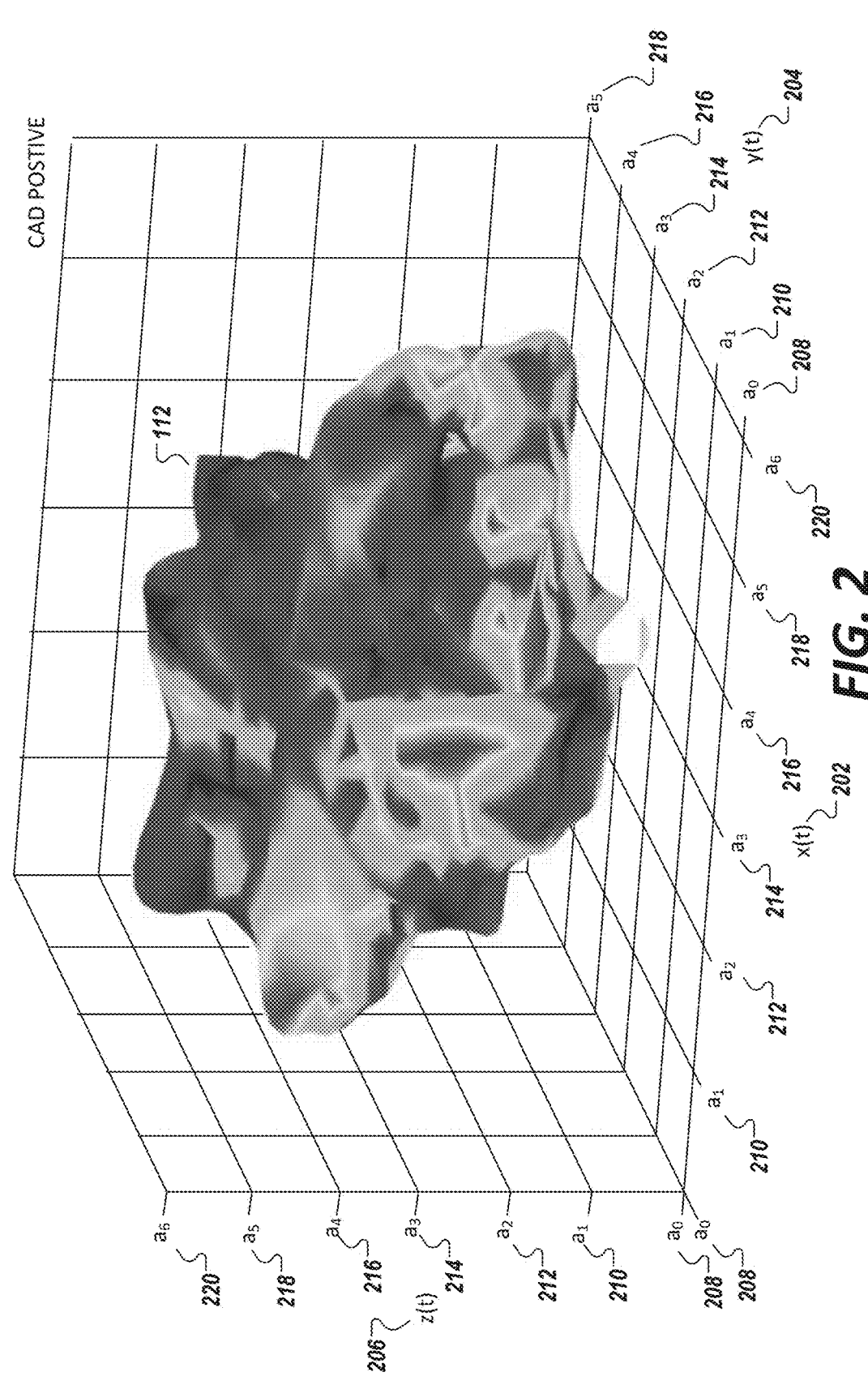
FIGS. 2 and 3 each shows a phase space volumetric object generated from a biophysical measurement of a subject determined to have significant coronary artery disease in accordance with an illustrative embodiment.
Figure 3:
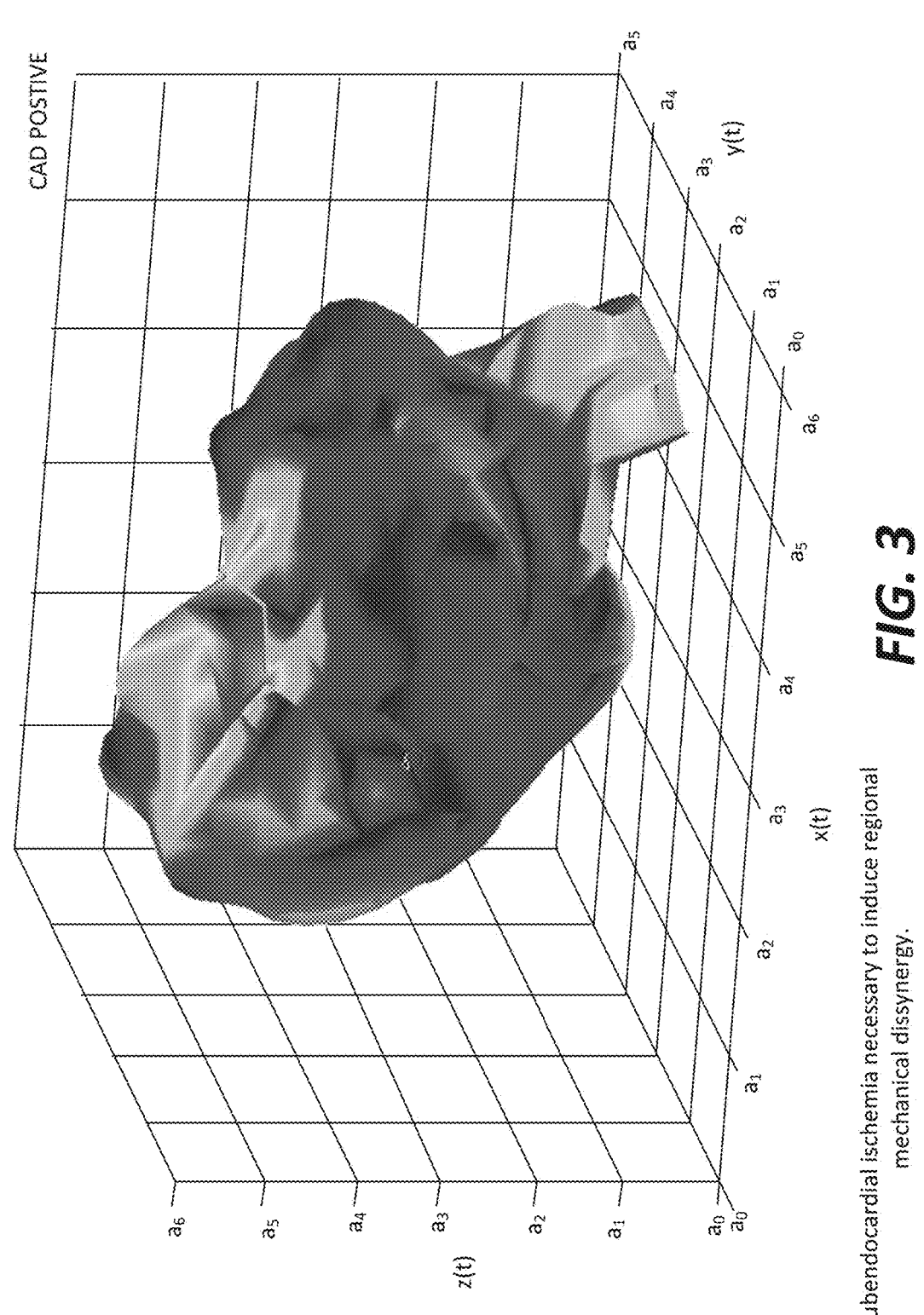

FIGS. 2 and 3 each shows a phase space volumetric object generated from a biophysical measurement of a subject determined to have significant coronary artery disease in accordance with an illustrative embodiment.

Given that computed phase space tomographic images are rendered images of the phase space volumetric object from a specific vantage and/or view, a phase space volumetric object can also be referred to as a computed phase space tomographic image. As shown in FIG. 2, each of the x-axis 202, y-axis 204, and z-axis 206 of the phase space volumetric object includes a set of fractional derivative orders associated with the fractional derivative operation performed on components of a subspace data set (e.g., the input data set, the model data set, or a model of the low-energy frequency subspace data set). The fractional derivative operation non-linearly preserves and enhances features of the subspace data set in different frequency bands. To this end, long cardiac phase gradient signals, existing as high-dimensional data due to the multiple acquisition leads, and exhibiting complex nonlinear variability, can be efficiently captured by this modeling techniques.

As shown in the example of FIG. 2, values of one or more fractional derivative orders are expressed in order at positions $a_0$ (208), $a_1$ (210), $a_2$ (212), $a_3$ (214), $a_4$ (216), $a_5$ (218), and $a_6$ (220) corresponding to indexed values of the low-energy frequency subspace data set. The orders are arranged, in some embodiments, in a sequence of ascending or descending values and are equally spaced apart from one another along each respective axis (202, 204, 206).

In some embodiments, the fractional derivative orders are pre-defined and may correspond to frequencies of electrical conduction events of the heart including those associated with activation (e.g., ventricular and/or atrio depolarization) of the various chambers and recovery (i.e., ventricular and/or atrio repolarization).

Indeed, the phase space volumetric object 112 provides a framework of aggregating multiple analyses (i.e., fractional derivative transform and low-energy frequency subspace analysis) of subspace data set that non-linearly preserves and enhances features in the low-energy frequency subspace data set in different frequency bands and representing these analyses, and/or the results thereof, as a three-dimensional volumetric object. In addition to being visually more distinct when rendered, it is observed that various topologic or geometric characteristics of the phase space volumetric object 112 can be readily extracted and/or determined to be used as predictors of presence or non-presence of significant coronary artery disease. In some embodiments, the extracted topologic or geometric characteristics include an assessed volume of the phase space volumetric object 112. In other embodiments, views of the phase space volumetric object can be presented as computed tomographic images that can be directly presented to a physician for evaluation.

In some embodiments, different fractional derivative orders may be used for different axes of the phase space model. In some embodiments, inputs from different sensor types may be fused in a single phase space model to which different sets of fractional derivative orders may be applied for each respective sensor type.

FIGS. 2 and 3 each shows a phase space volumetric object generated from a biophysical measurement of a subject known to be CAD positive—that is, the subject has been determined to have significant coronary artery disease.

Figure 4:
FIG. 4 shows a phase space volumetric object generated from a biophysical measurement of a subject known to be CAD determined not to have significant coronary artery disease in accordance with an illustrative embodiment.

FIG. 4 shows a phase space volumetric object generated from a biophysical measurement of a subject known to be CAD negative—that is, the subject has been determined not to have significant coronary artery disease. As shown, the volume of the phase space volumetric object 112 of FIG. 2 or 3 associated with a CAD-positive subject is substantially higher than that of the phase space volumetric object 112 of FIG. 4 associated with a CAD-negative subject.

In some embodiments, the extracted topologic or geometric characteristics include a determination of whether the phase space volumetric object 112 includes certain shaped structures (e.g., arc or open space). In some embodiments, the extracted topologic or geometric characteristics include a determination of whether the phase space volumetric object 112 includes a fragmentary volume (i.e., more than one contiguous volume).

Figure 5:
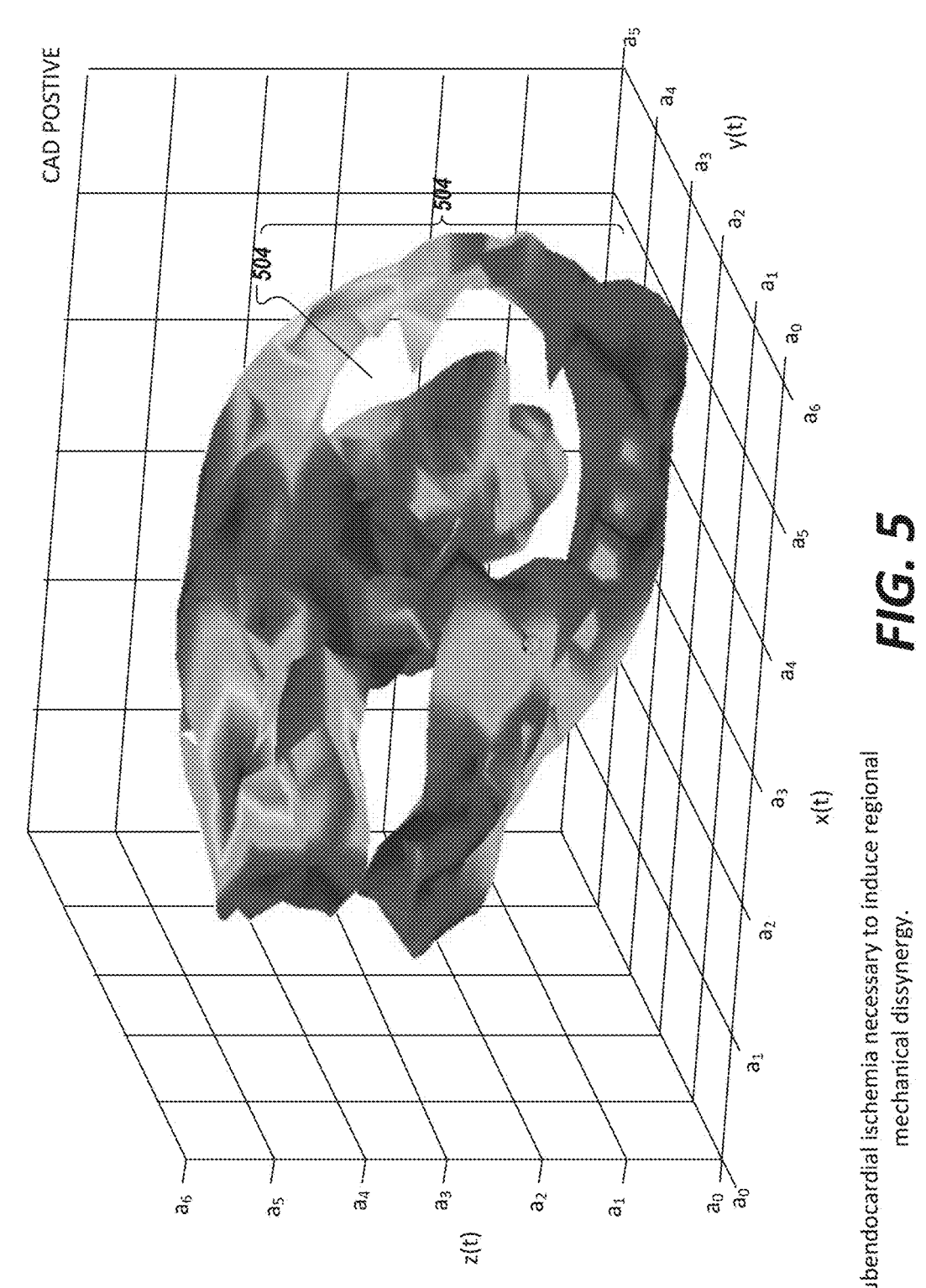
FIG. 5 shows a phase space volumetric object generated from a measurement of a subject determined to have significant coronary artery disease in which the object includes an arc structure that forms an open space in the object in accordance with an illustrative embodiment.

FIG. 5 shows a phase space volumetric object generated from a measurement of a subject known to be CAD positive in which the object 112 includes an arc structure 502 that forms an open space 504 in the object 112.

As shown in FIG. 2, in addition to structural components, in some embodiments, the phase space volumetric object 112 is configured with color map information that corresponds to additional dimension of analysis. In some embodiments, each vertex has one or more color values that are calculated as a variance between a modeled channel data set (e.g., X-axis data set, Y-axis data set, or Z-axis data set) a base-line raw channel data set (e.g., corresponding X-axis data set, Y-axis data set, or Z-axis data set). In some embodiments, the variance is determined by subtracting data points of the base-line raw channel data set with the corresponding data points of the modeled channel data set. The modeled channel data set, in some embodiments, is based on a sparse approximation of the base-line raw channel data set to generate a reconstructed noiseless signal of the base-line raw channel data. In some embodiments, each face of the phase space volumetric object 112 is assigned a face color value triangularly interpolated among neighboring bounding vertex color values (e.g., 3 bounding vertex colors).

Example Method to Construct a Phase Space Volumetric Object

FIG. 6 is an example method 600 of generating a phase space volumetric object 112 by the non-invasive cardiac assessment system 110 in accordance with an illustrative embodiment. The method 600 includes removing (operation 602) a baseline wander from the raw differential channel signal of phase-gradient biophysical data set 108. In some embodiments, the raw differential channel signal are derived from six signals simultaneously sampled by the measurement system 102.

In some embodiments, six simultaneously sampled signals are captured from a resting subject as the raw differential channel signal data set in which the signals embed the inter-lead timing and phase information of the acquired signals, specific to the subject. Geometrical contrast arising from the interference in the phase plane of the depolarization wave with the other orthogonal leads can be used which can facilitate superimposition of phase space information on a three-dimensional representation of the heart. Noiseless subspaces further facilitate the observation of the phase of these waves. That is, the phase of the orthogonal leads carries the information about the structure and generates geometrical contrast in the image. Phase-contrast takes advantage of the fact that different bioelectric structures have different impedances, and so spectral and non-spectral conduction delays and bends the trajectory of phase space orbit through the heart by different amounts. These small changes in trajectory can be normalized and quantified beat to beat and corrected for abnormal or poor lead placement, and the normalized phase space integrals can be mapped to a geometric mesh for visualization.

In some embodiments, the raw differential channel signal data set is normalized and baseline wander are removed using a modified moving average filter. For example, in some embodiments, the baseline wander is extracted from each of the raw differential channel signals using a median filter with an order of 1500 milliseconds, smoothed with a 1-Hz low-pass filter, and subtracted from the signals. The bias is then removed from the resulting signals by subtracting estimations of the signals using maximums of probability densities calculated with a kernel smoothing function. All of the signals may be divided by their respective interquartile ranges to complete the normalization process. In other embodiments, the baseline wander is removed using a phase-linear $2^{nd}$ order high-pass filter (e.g., a second-order forward-reverse high-pass filter having a cut-off frequency at 0.67 Hz). The forward and reverse operation ensures that the resulting pre-processed biophysical-signal data set 118 is phase-linear. Other phase-linear operations be used—e.g., based on wavelet filters, etc.

The method 600 then includes reconstructing (operation 604) a noiseless model signal by decomposing and selecting sets of candidate basis functions to create a sparse mathematical model. In some embodiments, a Modified Matching Pursuit (MMP) algorithm is used to find a noiseless model of the raw differential channel signals. Other sparse approximation algorithms can be used, including, and not limited to, evolvable mathematical models, symbolic regression, orthogonal matching pursuit, LASSO, linear models optimized using cyclical coordinate descent, orthogonal search, fast orthogonal search, and cyclical coordinate descent. In some embodiments, the reconstructing operation 604 generates a model as a function with a weighted sum of basis functions in which basis function terms are sequentially appends to an initially empty basis to approximate a target function while reducing the approximation error.

The method 600 then includes selecting (operation 606) subspace components (e.g., low energy frequency subspace components) from the selected basis functions and coefficients. The low-energy subspace components comprises a model reconstructed by using only the X % low magnitude subset coefficients (frequency content) contributing least to the modelling error. Low-energy subspace components, in some embodiments, includes higher order candidate terms that are later selected, in the phase space coordinates, as part of the sparse representation of a signal. That is, the last 5 percent, 10 percent, 15 percent, 20 percent, 25 percent, 30 percent of the candidate terms (as the higher order candidate terms) last selected via the sparse approximation is used. Other percentage values can be used. The low-energy frequency subspace components can be used to define the shape of the three-dimensional point cloud of the phase space volumetric object 112.

The method 600 then includes reconstructing (operation 608) a pre-defined set of n$^{th}$ order fractional derivative result set (e.g., via a numeric fractional derivative operation) to generate, for example, color parameters for the three-dimensional point cloud defining, in part, the phase space volumetric object 112. In some embodiments, the fractional derivative order is an irrational number. In some embodiments, more than one fractional derivative operation may be applied with different fractional derivative orders. In some embodiments, the fractional derivative operation is based on Grünwald-Letnikov fractional derivative method. In some embodiments, the fractional derivative operation is based on the Lubich's fractional linear multi-step method. In some embodiments, the fractional derivative operation is based on the fractional Adams-Moulton method. In some embodiments, the fractional derivative operation is based on the Riemann-Liouville fractional derivative method. In some embodiments, the fractional derivative operation is based on Riesz fractional derivative method. Other methods of performing a fractional derivative may be used.

The method 600 then includes, in some embodiments, performing (610) triangulation operation to generate surface features (i.e., face) of the point cloud. In some embodiments, Alpha Hull triangulation with a pre-predetermined radius ($\alpha$) is performed on the reconstructed noiseless model signals. In other embodiments, Delaunay triangulation, alpha shapes, ball pivoting, Mesh generation, Convex Hull triangulation, and the like, is used.

The method 600 then includes, in some embodiments, computing (612) one or more values for each of the vertices in the point cloud. The vertex values, in some embodiments, are scaled over a presentable color range. The vertex values, in some embodiments, is a variance between a modeled channel data set (e.g., X-axis data set, Y-axis data set, or Z-axis data set) a base-line raw channel data set (e.g., corresponding X-axis data set, Y-axis data set, or Z-axis data set). In some embodiments, the variance is determined by subtracting data points of the base-line raw channel data set with the corresponding data points of the modeled channel data set. The modeled channel data set, in some embodiments, is based on a sparse approximation of the base-line raw channel data set to generate a reconstructed noiseless signal of the base-line raw channel data. In some embodiments, each face of the phase space volumetric object 112 is assigned a face color value triangularly interpolated among neighboring bounding vertex color values (e.g., 3 bounding vertex colors).

In some embodiments, various views of the phase space volumetric object 112 are captured for presentation as computed phase space tomographic images, e.g., via a web portal, to a physician to assist the physician in the assessment of presence or non-presence of significant coronary artery disease. In some embodiments, the phase space volumetric object or the computed phase space tomographic images are assessed by a trained neural network classifier configured to assess for presence or non-presence of significant coronary artery disease. In some embodiments, the computed tomographic images are presented alongside the results of a machine-generated predictions to assist in the physician in making a diagnosis.

In other embodiments, the phase space volumetric object 112 is analyzed in subsequent machine learning operations (e.g., image-based machine learning operations or feature-based machine learning operations) to determine the one or more coronary physiological parameters. In some embodiments, the assessment system 110 is configured to determine a volume metric (e.g., alpha hull volume) of the phase space volumetric object 112. In some embodiments, the assessment system 110 is configured to determine a number of distinct bodies (e.g., distinct volumes) of the generated phase space volumetric object 112. In some embodiments, the assessment system 110 is configured to assess a maximal color variation (e.g., color gradient) of the generated phase space volumetric object 112. In some embodiments, all these features are assessed from phase space volumetric object 112 as a mathematical feature.

In some embodiments, the mathematical features of the phase space volumetric object 112 are extracted along with hundreds of other distinct mathematical features that represent specific aspects of the biophysical signals collected. A feature extraction engine of the assessment system 110 may extract each feature as a specific formula/algorithm. In some embodiments, when the feature extraction process is applied to an incoming biophysical signal, the output is a matrix of all calculated features which includes a list, for example, of over hundreds of real numbers; one number per feature in which each feature represents one or more aspects of the signal's dynamical, geometrical, fractional calculus, chaotic, and/or topological properties.

A machine learning algorithm (e.g., meta-genetic algorithm), in some embodiments, is used to generate predictors linking aspects of the phase space model (e.g., pool of features) across a population of patients representing both positive (i.e., have disease) and negative (i.e., do not have disease) cases to detect the presence of myocardial tissue associated with significant coronary artery disease. In some embodiments, the performances of the candidate predictors are evaluated through a verification process against a previously unseen pool of patients. In some embodiments, the machine learning algorithm invokes a meta-genetic algorithm to automatically select a subset of features drawn from a large pool. This feature subset is then used by an Adaptive Boosting (AdaBoost) algorithm to generate predictors to diagnose significant coronary artery disease across a population of patients representing both positive and negative cases. The performances of the candidate predictors are determined through verification against a previously unseen pool of patients. A further description of the AdaBoost algorithm is provided in Freund, Yoav, and Robert E. Schapire, "A decision-theoretic generalization of on-line learning and an application to boosting," European conference on computational learning theory. Springer, Berlin, Heidelberg (1995), which is incorporated by reference herein in its entirety.

In some embodiments, the system 100 generates one or more images of a representation of the phase space volumetric object 112 in which the vertices, face triangulations, and vertex colors are presented. In some embodiments, multiple views of the representation is generated and included in a report. In some embodiments, the one or more images are presented as a three-dimensional object that can be rotated, scaled, and/or panned based on user's inputs. Indeed, such presentation can be used to be assessed visually by a skilled operator to determine whether a subject has presence of non-presence of significant coronary artery disease.

It can be seen from the example images presented in FIGS. 8-21 that visual features of the phase space volumetric object 112 can be used to distinguish between both presence/absence of significant CAD and also degrees of CAD. Specifically the presence of fragmentary volumes and complete arcs from the primary (central) body of the image appear to be highly indicative of significant CAD. The degree of coloration is also of interest, but harder to interpret manually. It can also been seen that there is an emergent phenomena whereby subjects with blockages that are classed as non-significant appear to be developing geometric features prototypical of the arcs and fragmentation that indicate the presence of significant CAD.

Experimental Results of Feature-Extracted Machine Learning

A Coronary Artery Disease-Learning Algorithm Development (CADLAD) Study is currently being untaken that involves two distinct stages to support the development and testing of the machine-learned algorithms. In Stage 1 of the CADLAD study, paired clinical data is being used to guide the design and development of the pre-processing, feature extraction and machine learning steps. That is, the collected clinical study data is split into three cohorts: Training (50%), validation (25%), and verification (25%). Similar to the steps described above for processing signals from a patient for analysis, each signal is first pre-processed, to clean and normalize the data. Following these processes, a set of features are extracted from the signals in which each set of features is paired with a representation of the true condition—for example, the binary classification of the presence or absence of significant CAD. The final output of this stage is a fixed algorithm embodied within a measurement system. In Stage 2 of the CADLAD study, the machine-learned algorithms were used to provide a determination of significant CAD against a pool of previously untested clinical data. The criteria for disease was established as that defined in the American College of Cardiology (ACC) clinical guidelines, specifically as greater than 70% stenosis by angiography or less than 0.80 fraction-flow by flow wire.

In an aspect of the CADLAD study, an assessment system was developed that automatically and iteratively explores combinations of features in various functional permutations with the aim of finding those combinations which can successfully match a prediction based on the features. To avoid overfitting of the solutions to the training data, the validation set is used as a comparator. Once candidate predictors have been developed, they are then manually applied to a verification data set to assess the predictor performance against data that has not been used at all to generate the predictor. Provided that the data sets are sufficiently large, the performance of a selected predictor against the verification set will be close to the performance of that predictor against new data.

In an aspect of the CADLAD study, FIGS. 8-21 each shows an image of a representation of a phase space volumetric object 112 generated from a signal collected from a set of subjects in the CADLAD study in accordance with an illustrative embodiment. The subjects were selected at random from the CADLAD study and were evenly distributed across 4 classes: (1) subjects with no reported arterial blockages; (2) subjects with one or more blockages between 50% and 65%; (3) subjects with at least one blockage greater than 70%; and (4) subjects with multiple blockages greater than 70%.

Figure 8:
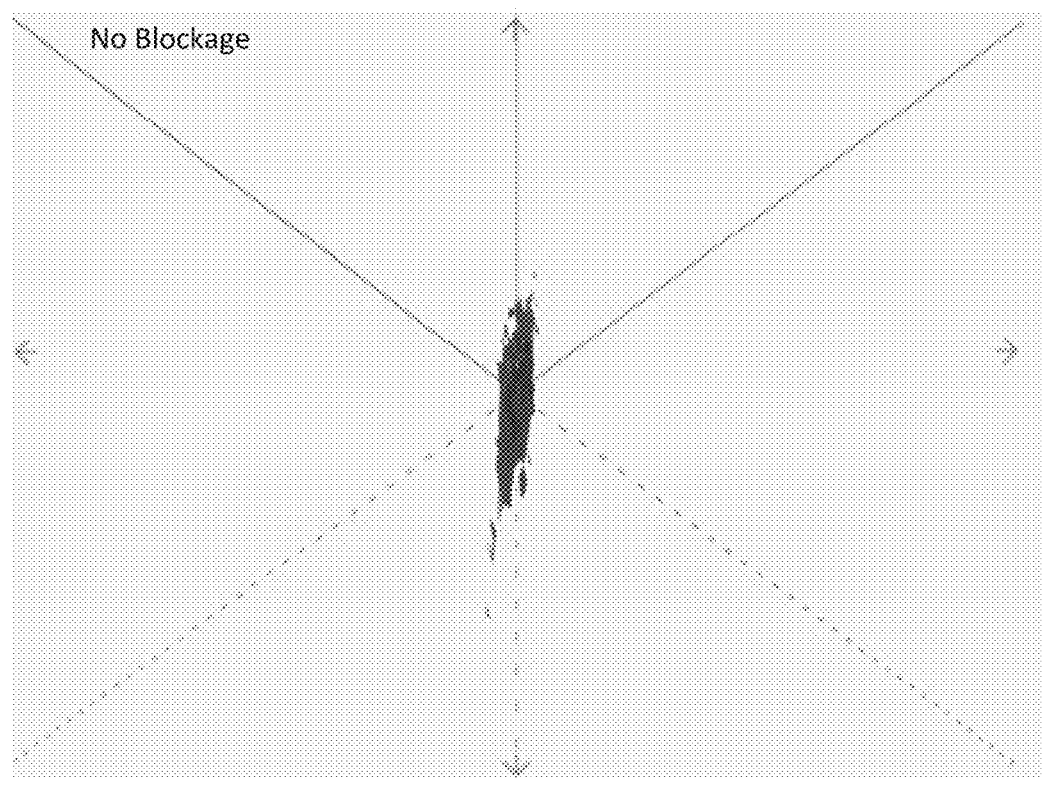
FIG. 8 shows an image of a representation of a phase space volumetric object generated from a signal collected from subject with no reported arterial blockage in accordance with an illustrative embodiment.

FIG. 8 shows an image of a representation of a phase space volumetric object 112 generated from a signal collected from subject with no reported arterial blockage in accordance with an illustrative embodiment. As can be seen, fractional derivative operations of a data set acquired from a healthy subject (i.e., without coronary artery disease) at most frequencies under study (i.e., fractional derivative order) yield minimal amplification of the underlying signal that effectively produce a phase space volumetric object 112 with a low and contiguous volume.

Figure 9:
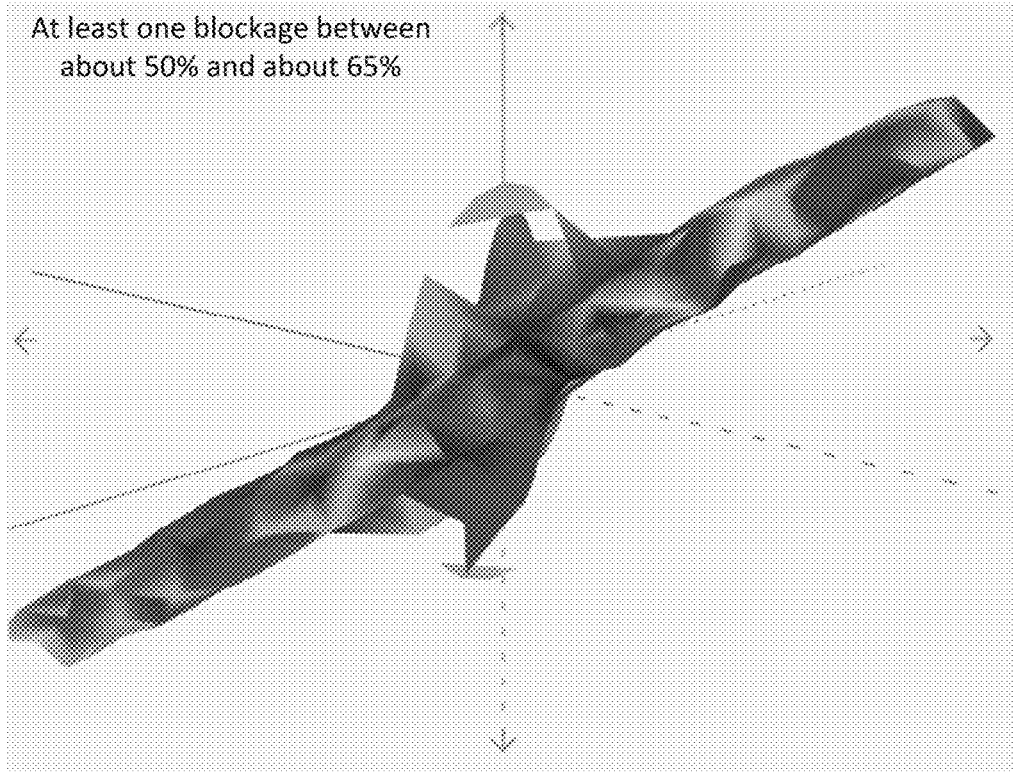
FIGS. 9, 10, and 11 each shows an image of a representation of a phase space volumetric object generated from a signal collected from a subject diagnosed with one or more reported arterial blockages only between about 50% and about 65% in accordance with an illustrative embodiment.
Figure 10:
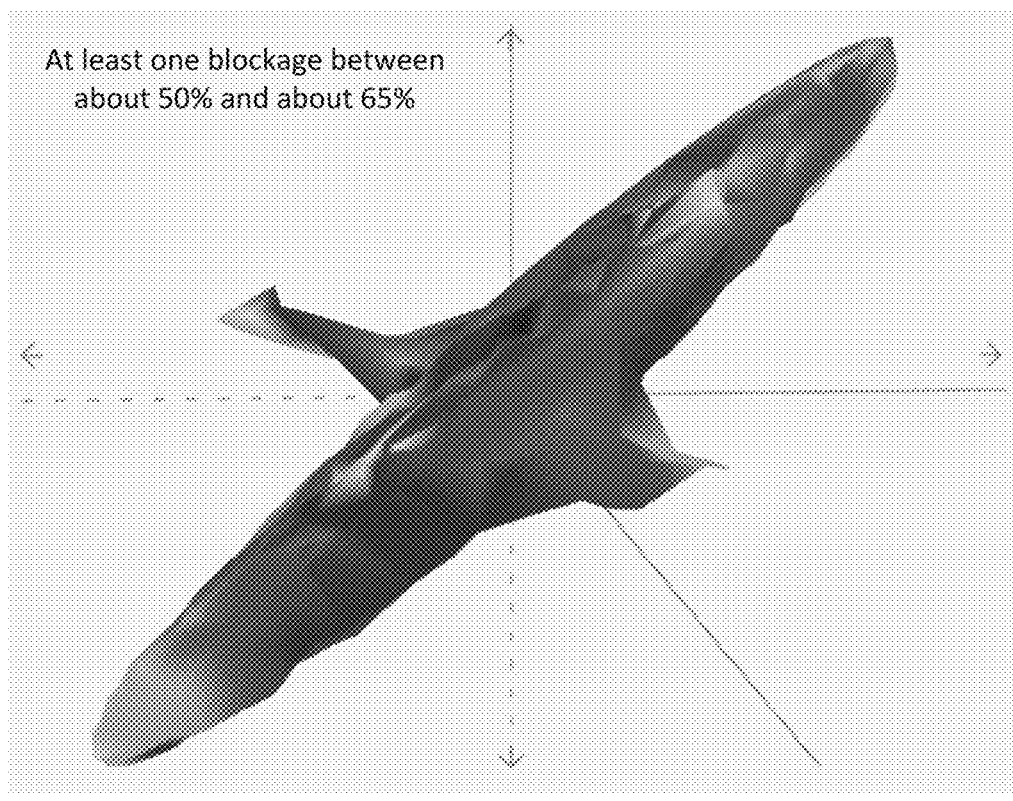
Figure 11:
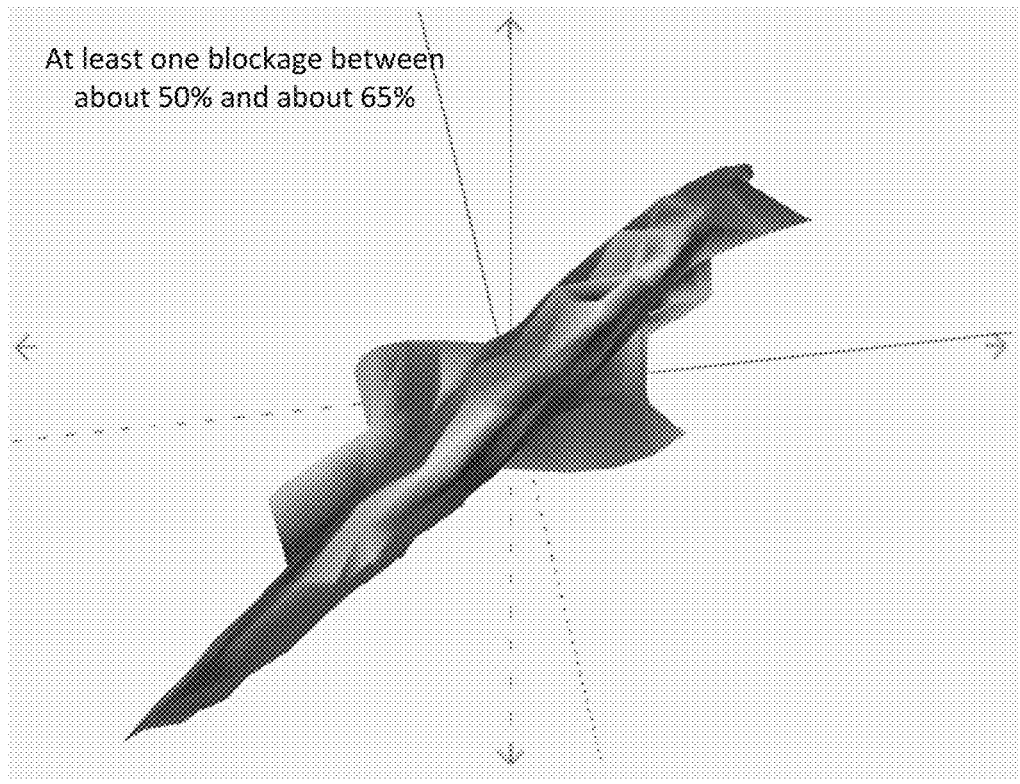
Figure 12:
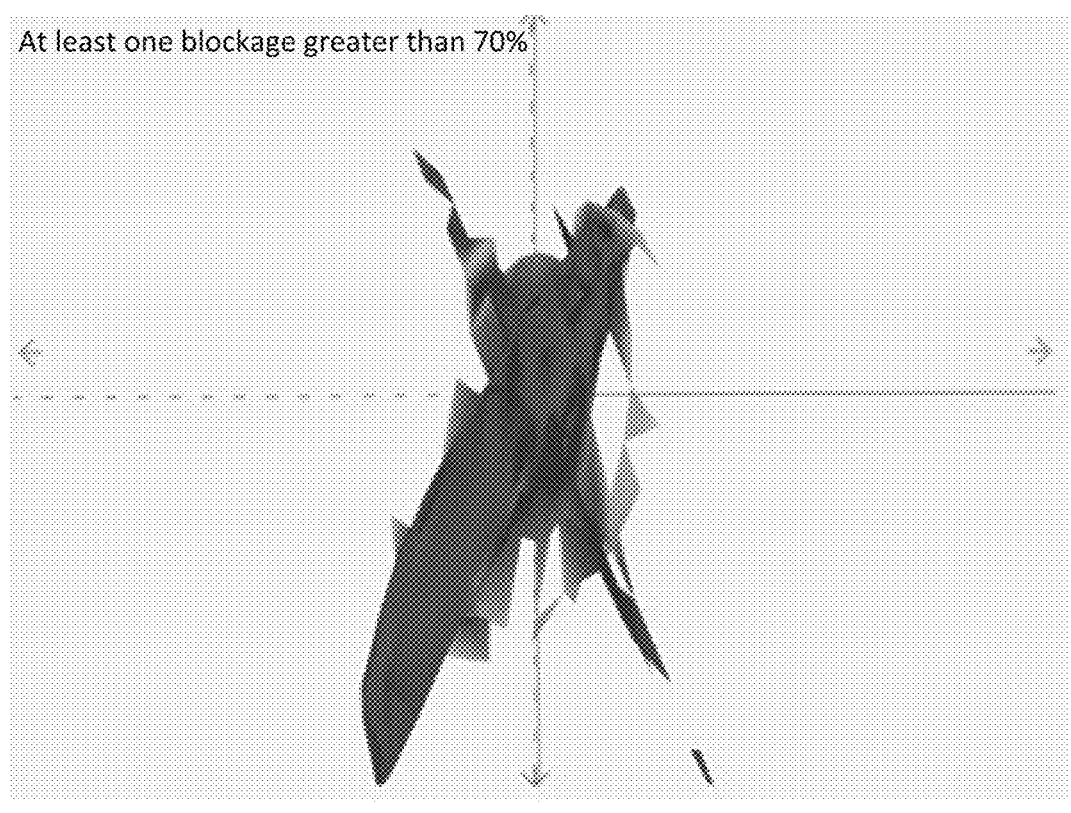
FIGS. 12, 13, 14, 15, and 16 each shows an image of a representation of a phase space volumetric object generated from a signal collected from a subject diagnosed with at least one reported arterial blockage greater than 70% in accordance with an illustrative embodiment.
Figure 13:
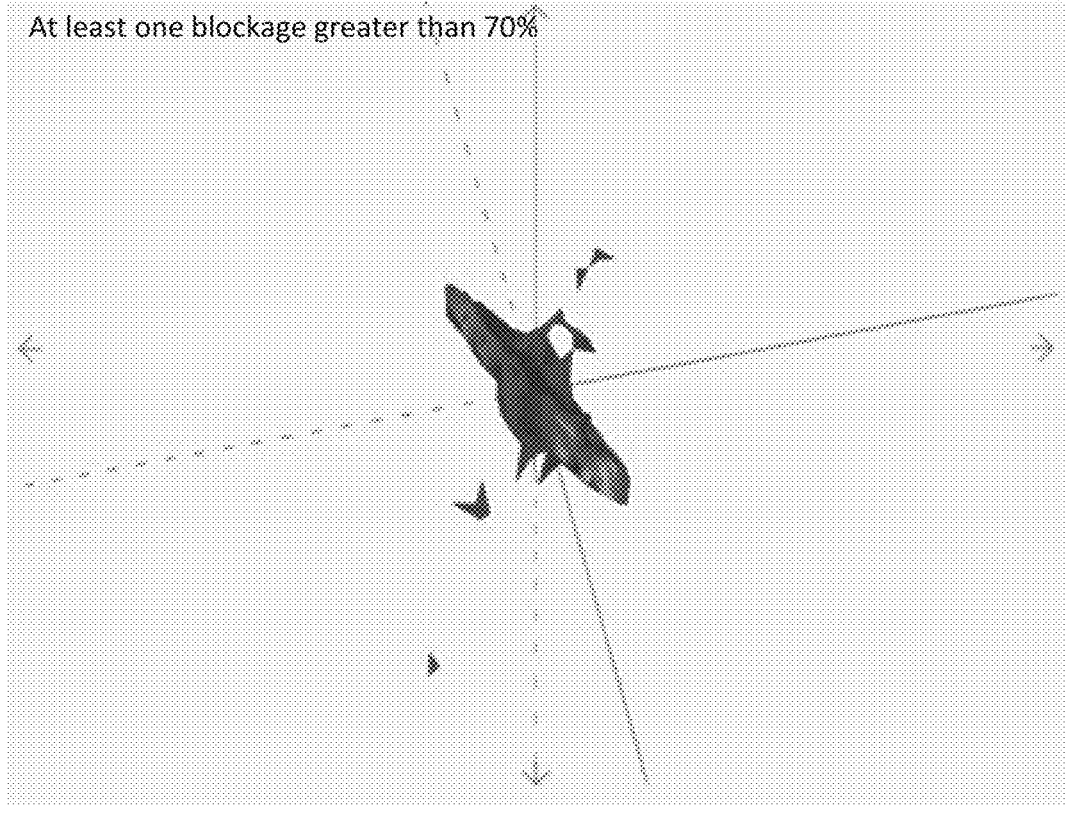
Figure 14:
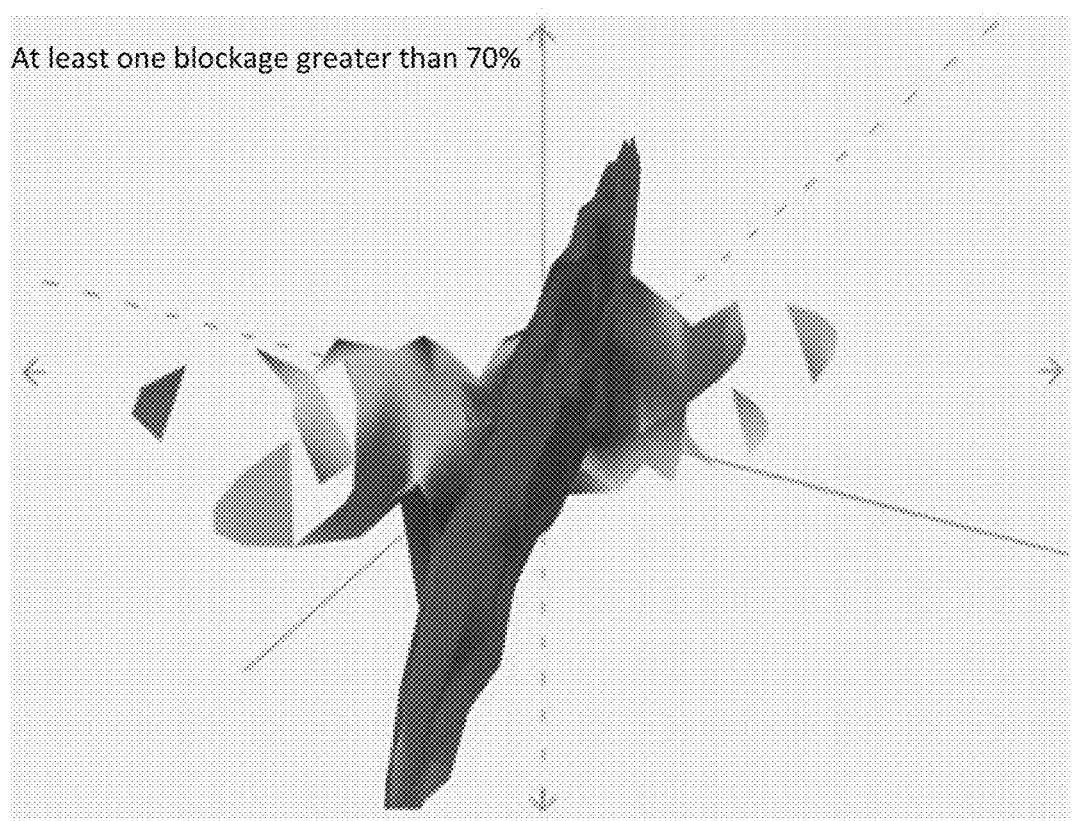
Figure 15:
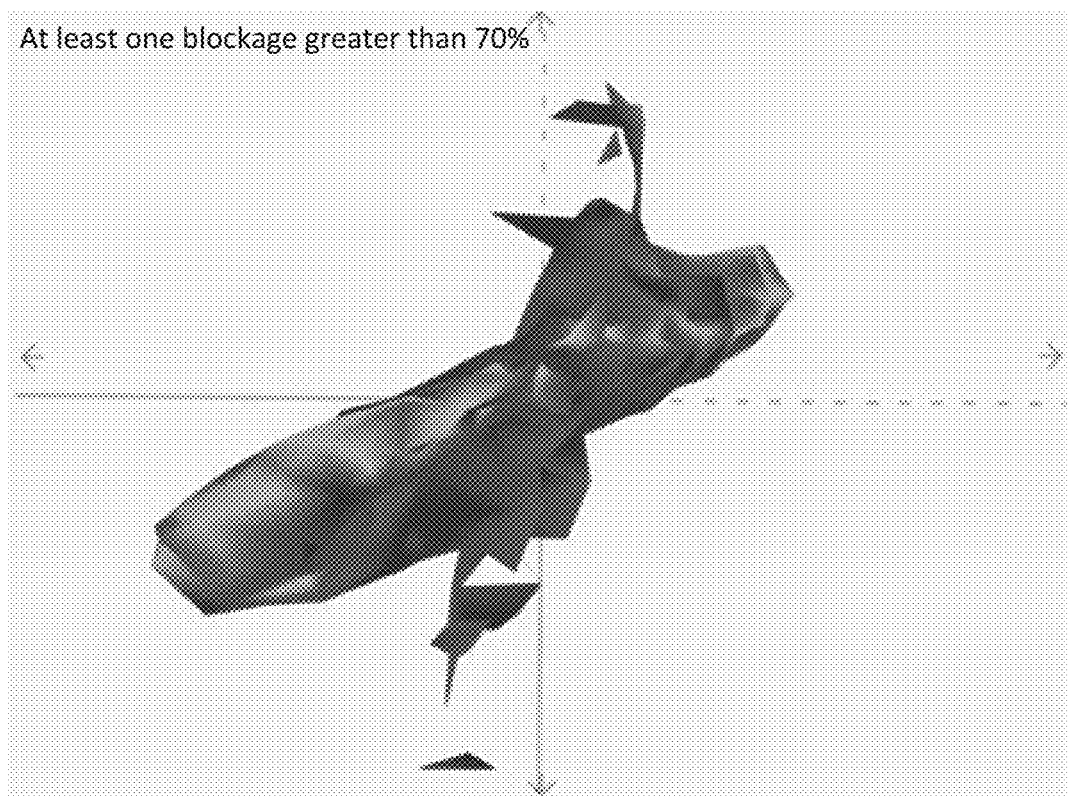
Figure 16:
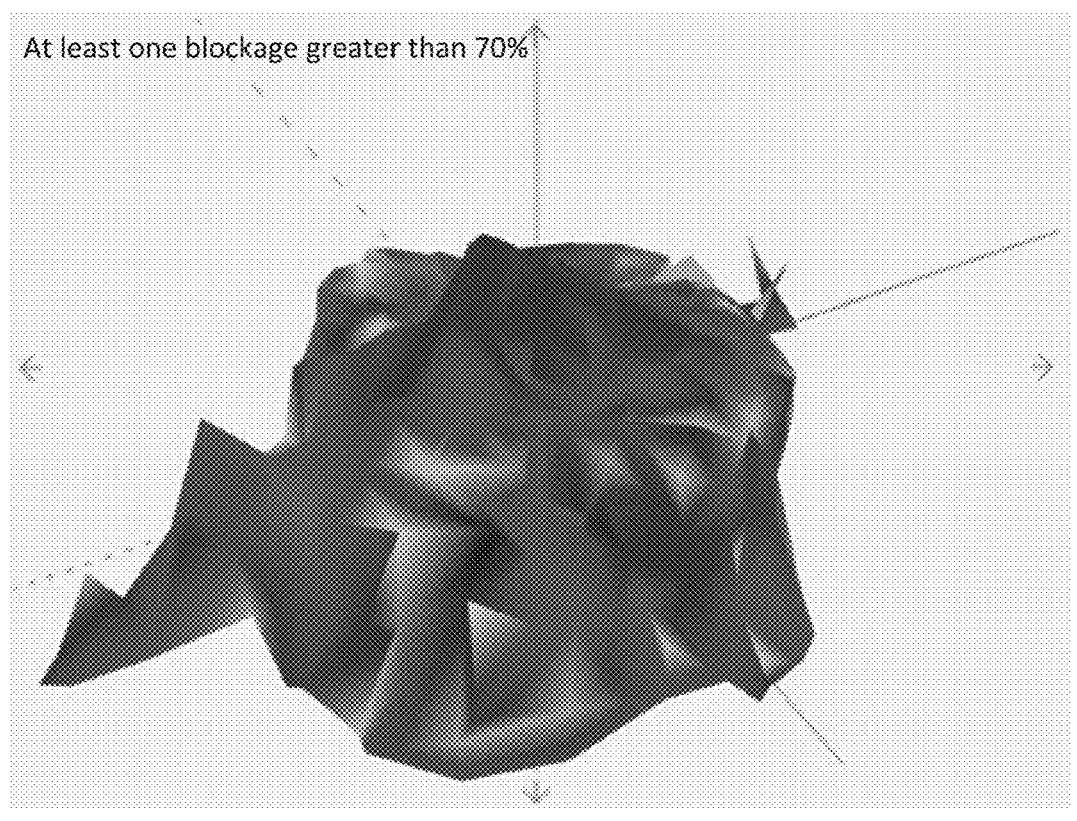
Figure 17:
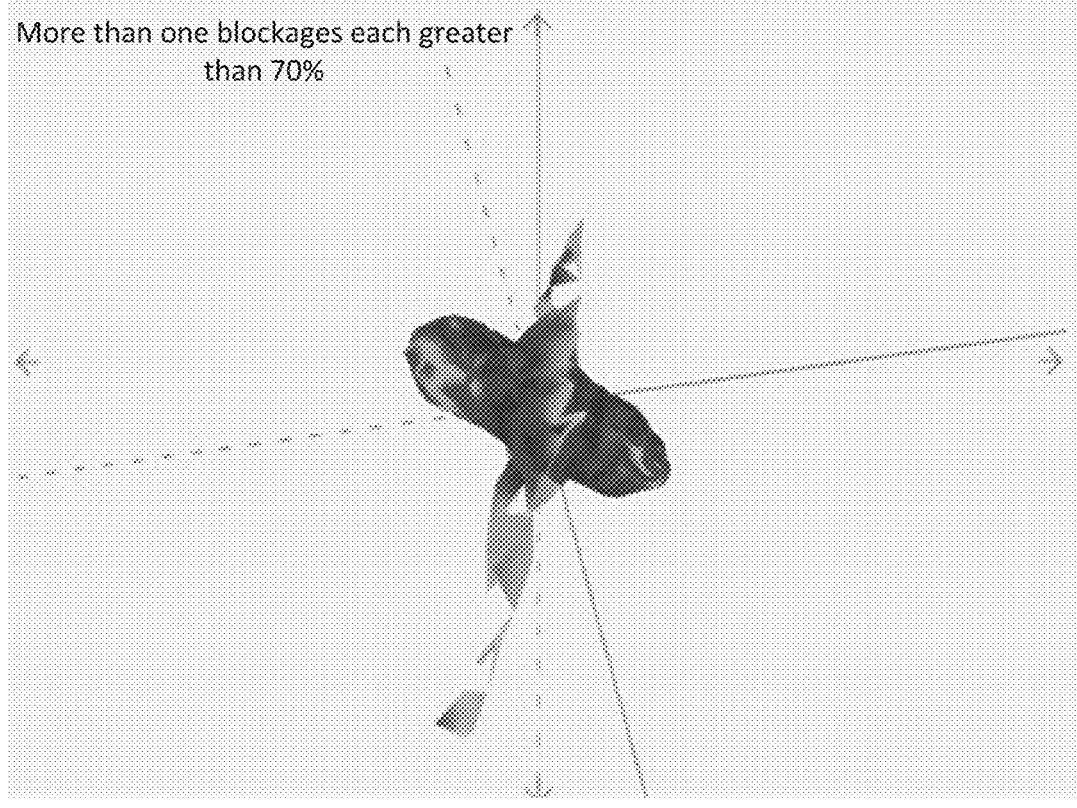
FIGS. 17, 18, 19, 20, and 21 each shows an image of a representation of a phase space volumetric object generated from a signal collected from a subject diagnosed with more than one reported arterial blockage each greater than 70% in accordance with an illustrative embodiment.
Figure 18:
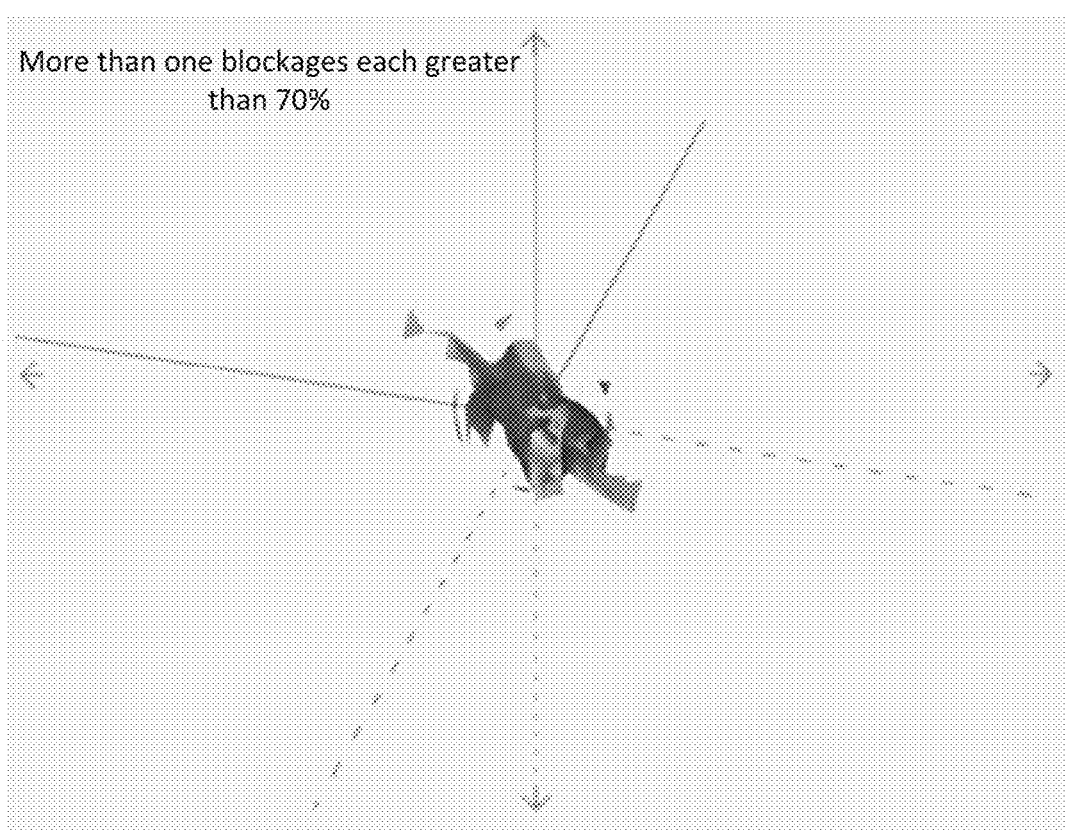
Figure 19:
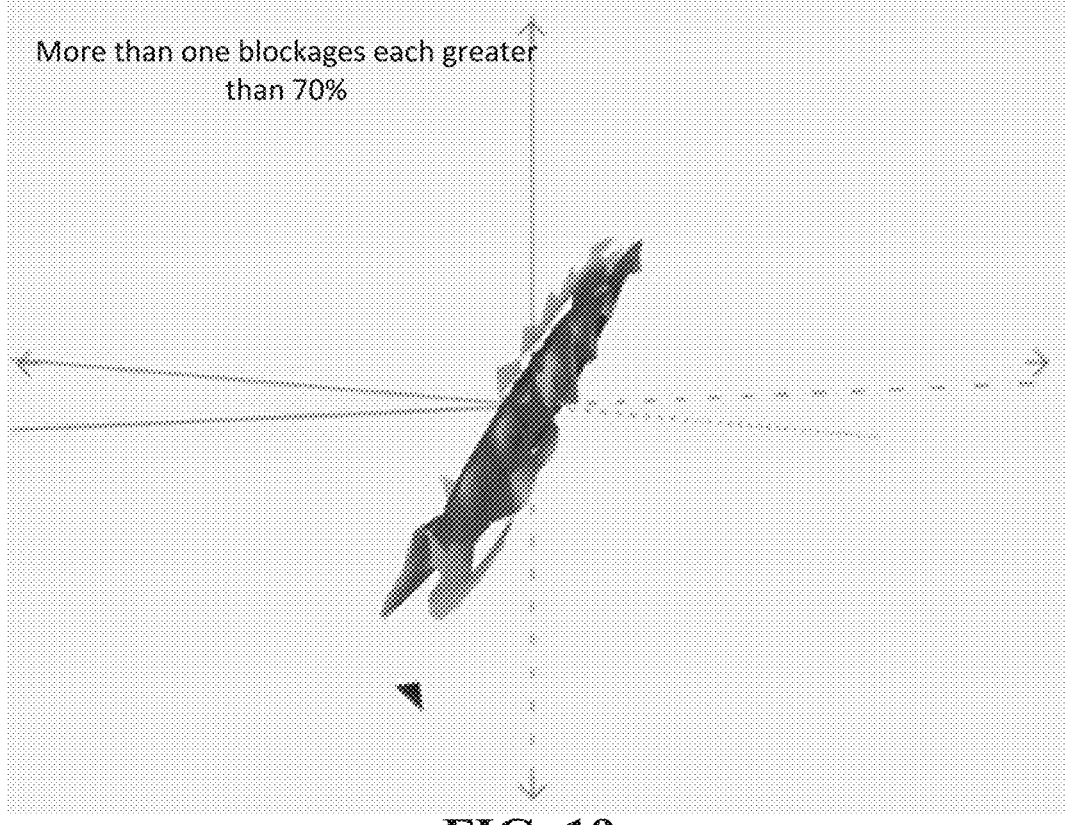
Figure 20:
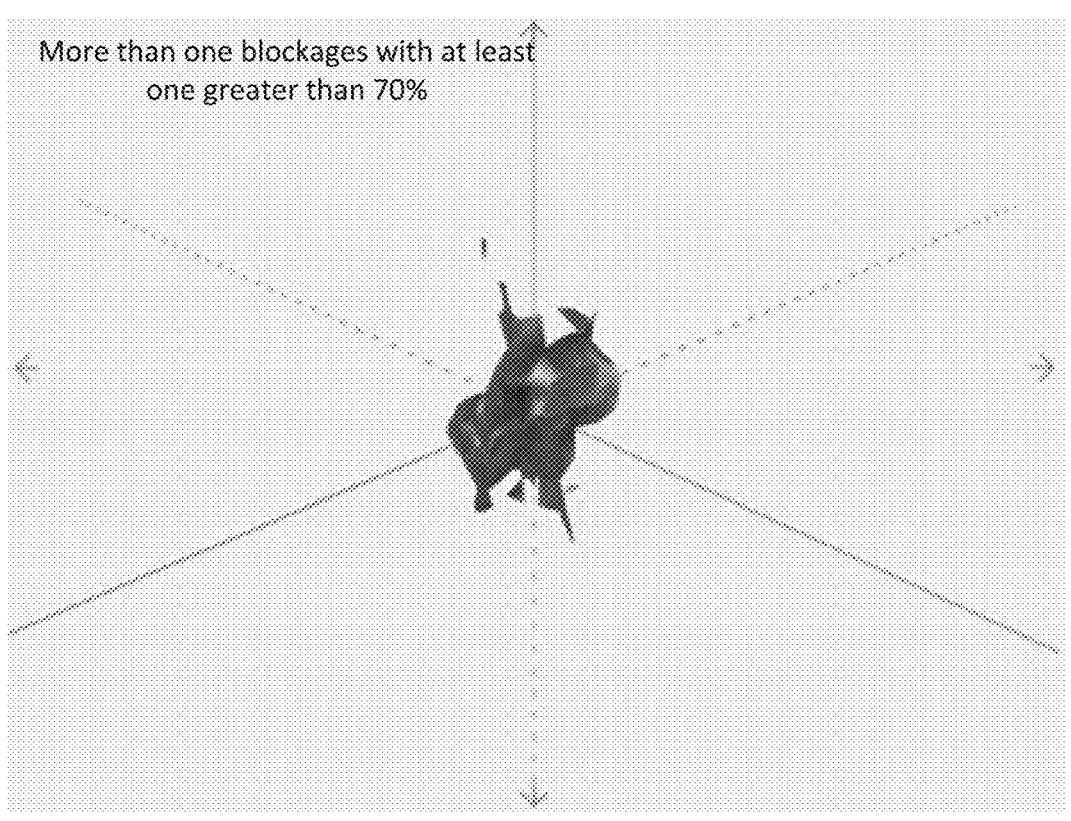
Figure 21:
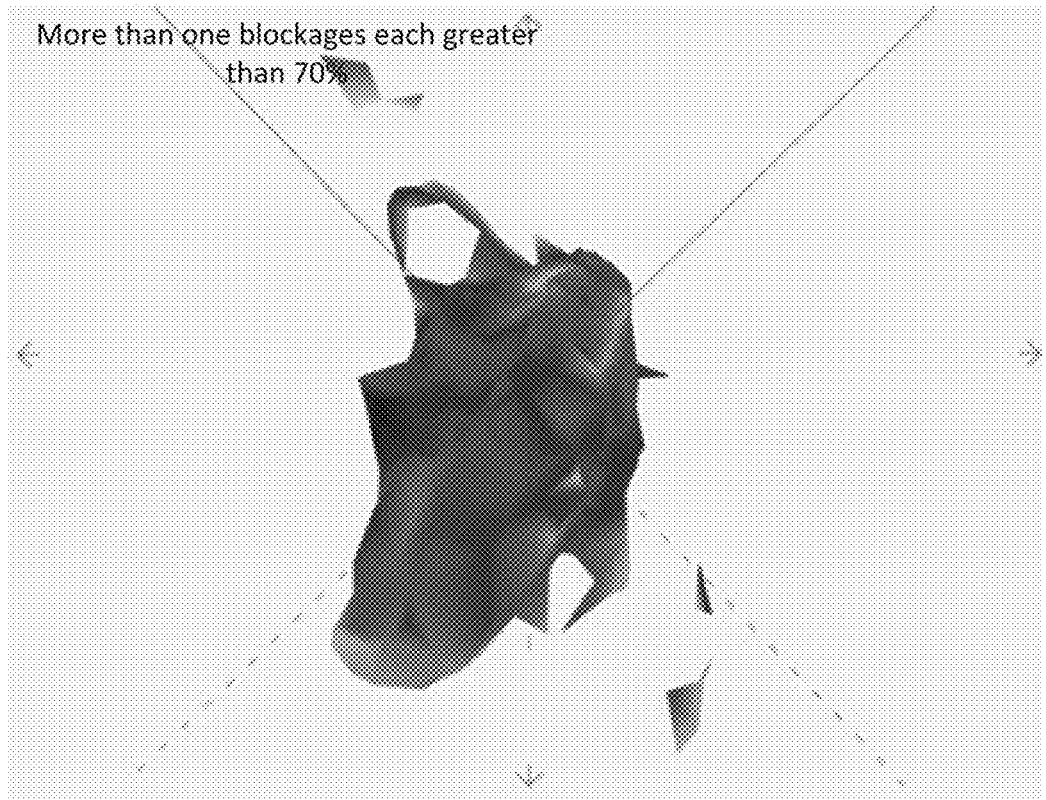

FIGS. 9, 10, and 11 each shows an image of a representation of a phase space volumetric object 112 generated from a signal collected from a subject diagnosed with one or more reported arterial blockages only between about 50% and about 65% in accordance with an illustrative embodiment. In contrast to FIG. 8, the fractional derivative operations of a data set acquired from a non-healthy subject (i.e., diagnosed with coronary artery disease) at most, or some, frequencies under study (i.e., fractional derivative order) yield amplification of the underlying signal that effectively produce a phase space volumetric object 112 with a larger and/or non-contiguous/fragmented volume.

FIGS. 12, 13, 14, 15, and 16 each shows an image of a representation of a phase space volumetric object 112 generated from a signal collected from a subject diagnosed with at least one reported arterial blockage greater than 70% in accordance with an illustrative embodiment.

FIGS. 17, 18, 19, 20, and 21 each shows an image of a representation of a phase space volumetric object 112 generated from a signal collected from a subject diagnosed with more than one reported arterial blockage each greater than 70% in accordance with an illustrative embodiment.

Cardiac Phase Space Tomography

As noted above, computed tomographic images that the physician can themselves interpret, can be produced based on the phase-space volumetric object. In some embodiments, the phase space volumetric objects 112 are used to generate a set of two dimensional views as the computed phase space tomographic images which can be directly interpreted, e.g., by a physician or by a machine learned classifier to assess for presence or non-presence of significant coronary artery disease. In certain implementations, a machine learned classifier has been observed to achieve a ROC (receiver operating characteristics) of 0.68 (0.49, 0.82) in which significant coronary artery disease is defined as greater than 70% stenosis by angiography or less than 0.80 fraction flow-by-flow wire.

Figures 22A, 22B, 22C, 22D, 22E, 22F:
FIGS. 22A, 22B, 22C, 22D, 22E, and 22F show a set of computed phase-space tomographic images derived from different views of the phase space volumetric object associated with a healthy subject in accordance with an illustrative embodiment.
Figures 23A, 23B, 23C, 23D, 23E, 23F:
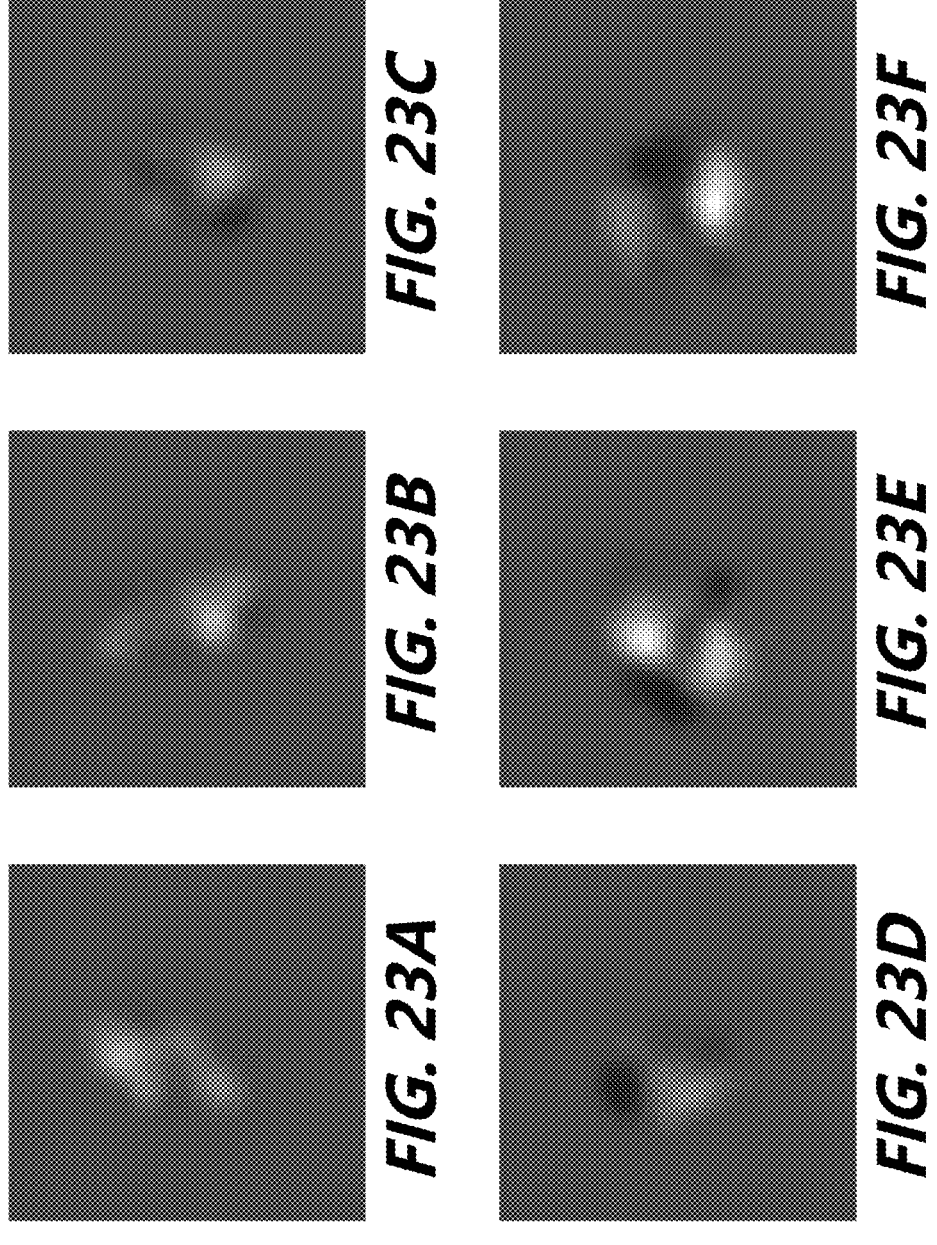
FIGS. 23A, 23B, 23C, 23D, 23E, and 23F show outputted classification of the tomographic images of FIGS. 22A-22F for presence and non-presence of significant coronary artery disease determined via a neural network classifier, in accordance with an illustrative embodiment.
Figures 24A, 24B, 24C, 24D, 24E, 24F:
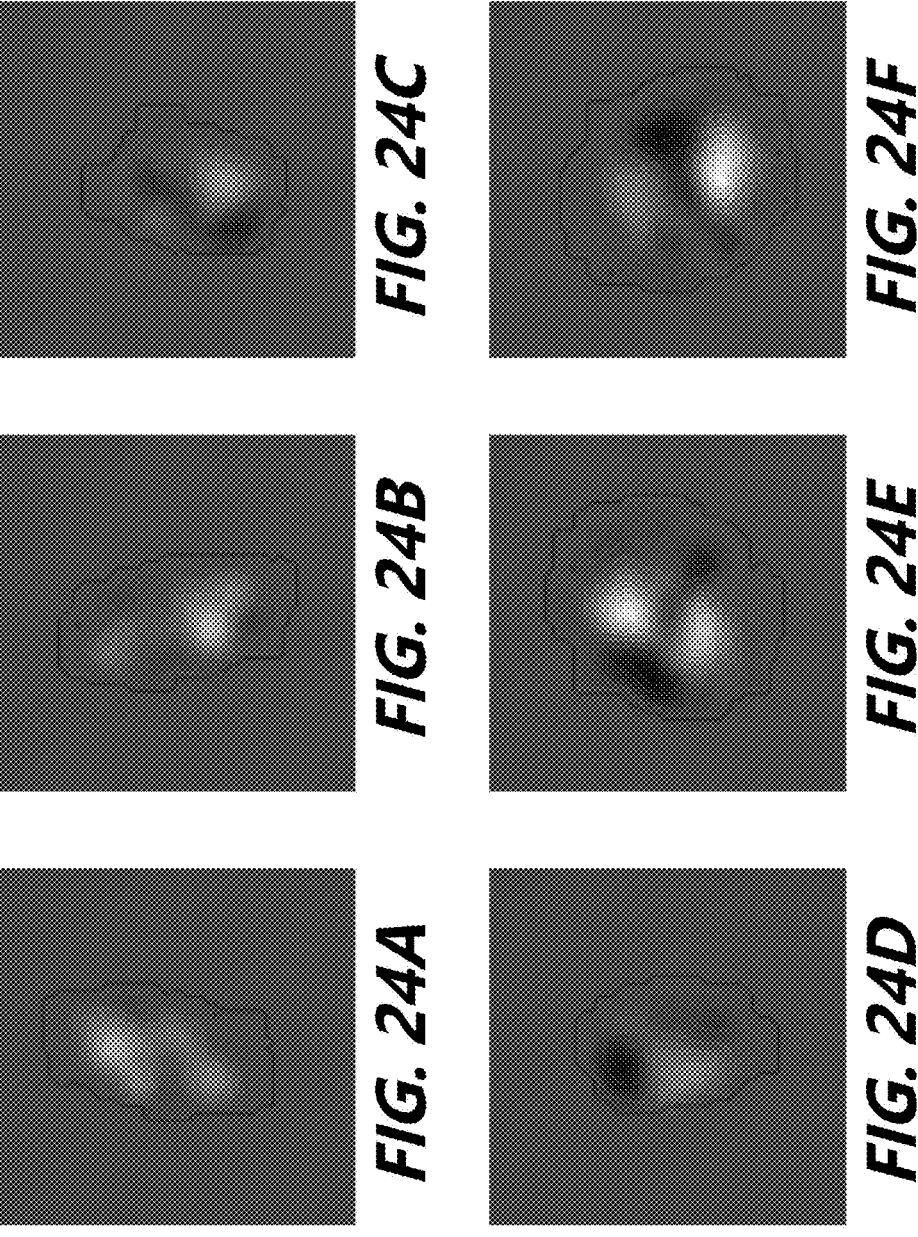
FIGS. 24A, 24B, 24C, 24D, 24E, and 24F show the outputted classification of the tomographic images of FIGS. 22A-22F overlaid with a contour data set and heat map associated with the classifier in accordance with an illustrative embodiment.
Figures 25A, 25B, 25C, 25D, 25E, 25F:
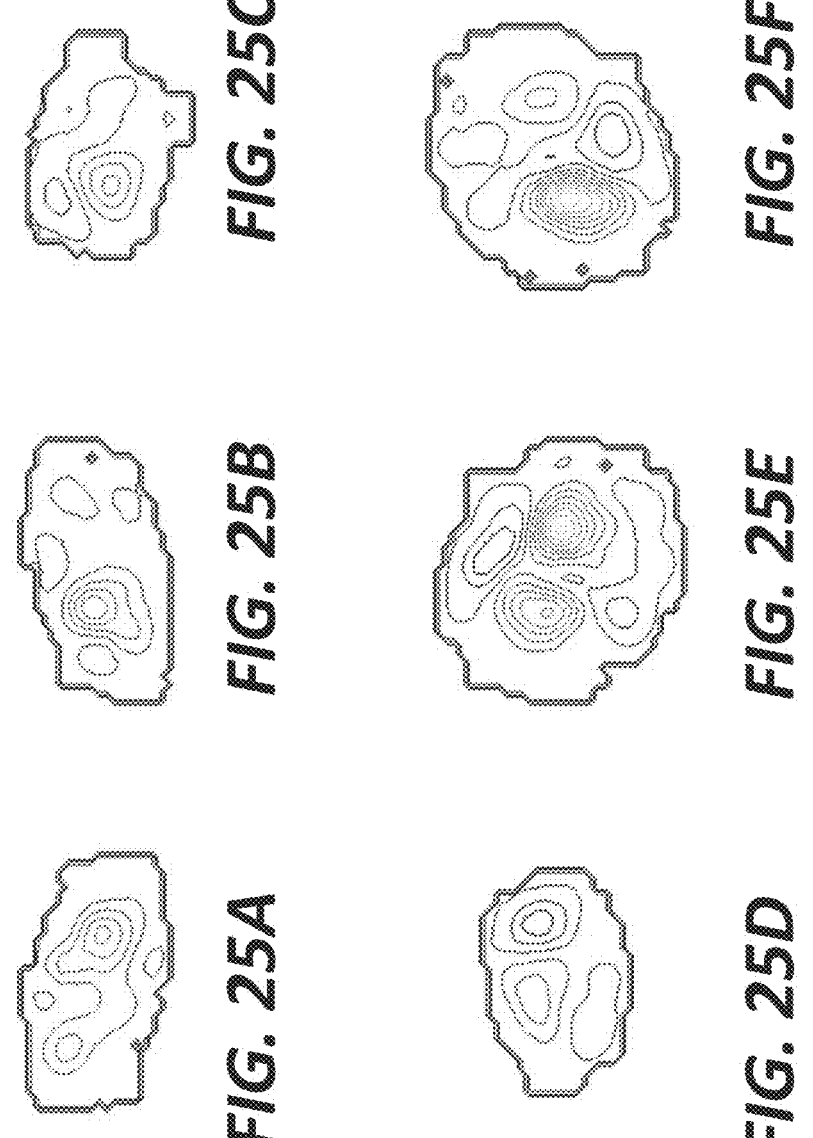
FIGS. 25A, 25B, 25C, 25D, 25E, and 25F show only the contour data set and heat map of FIGS. 24A-24F in accordance with an illustrative embodiment.
Figures 26A, 26B, 26C, 26D, 26E, 26F:
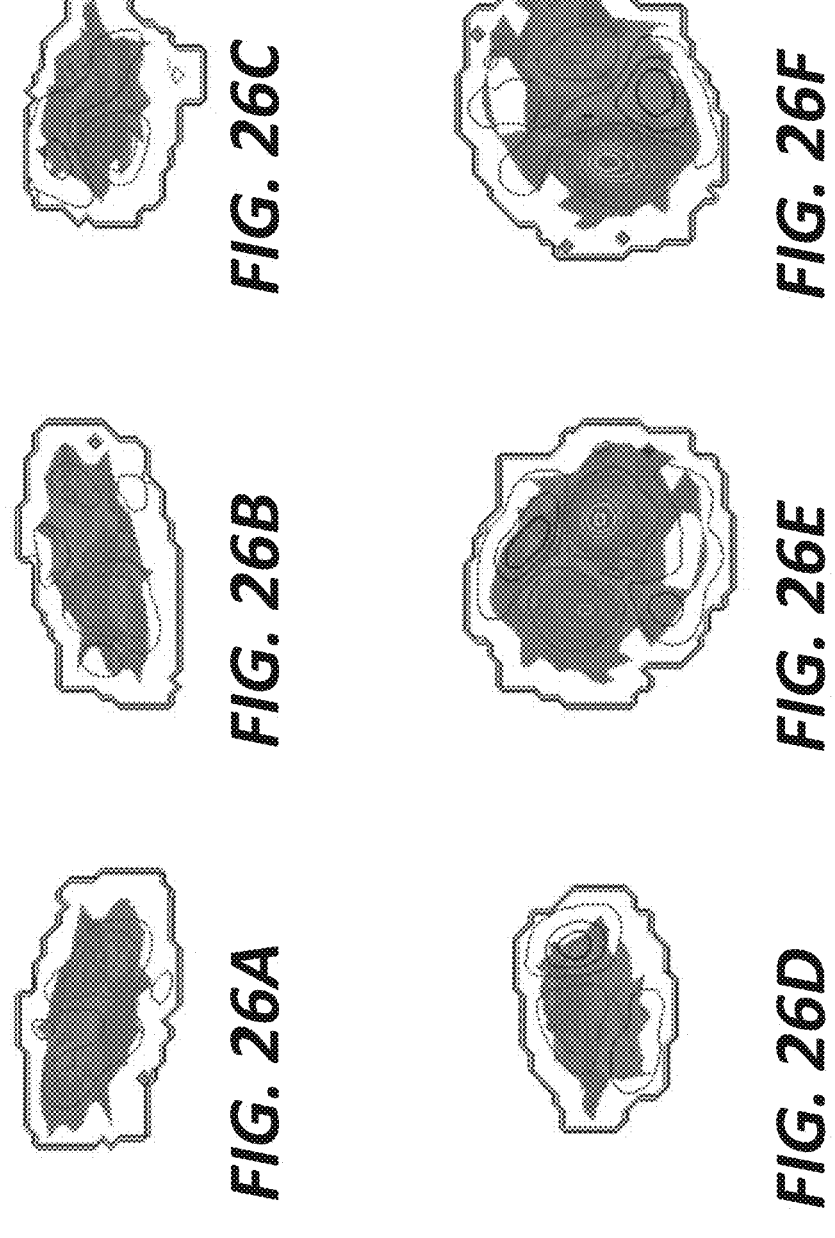
FIGS. 26A, 26B, 26C, 26D, 26E, and 26F show computed phase-space tomographic images derived from different views of the phase space volumetric object 112 and overlaid with the contour data set and heat map data set generated from the neural network classifier of FIGS. 25A-25F in accordance with an illustrative embodiment.
Figures 27A, 27B, 27C, 27D, 27E, 27F, 28A, 28B, 28C, 28D, 28E, 28F:
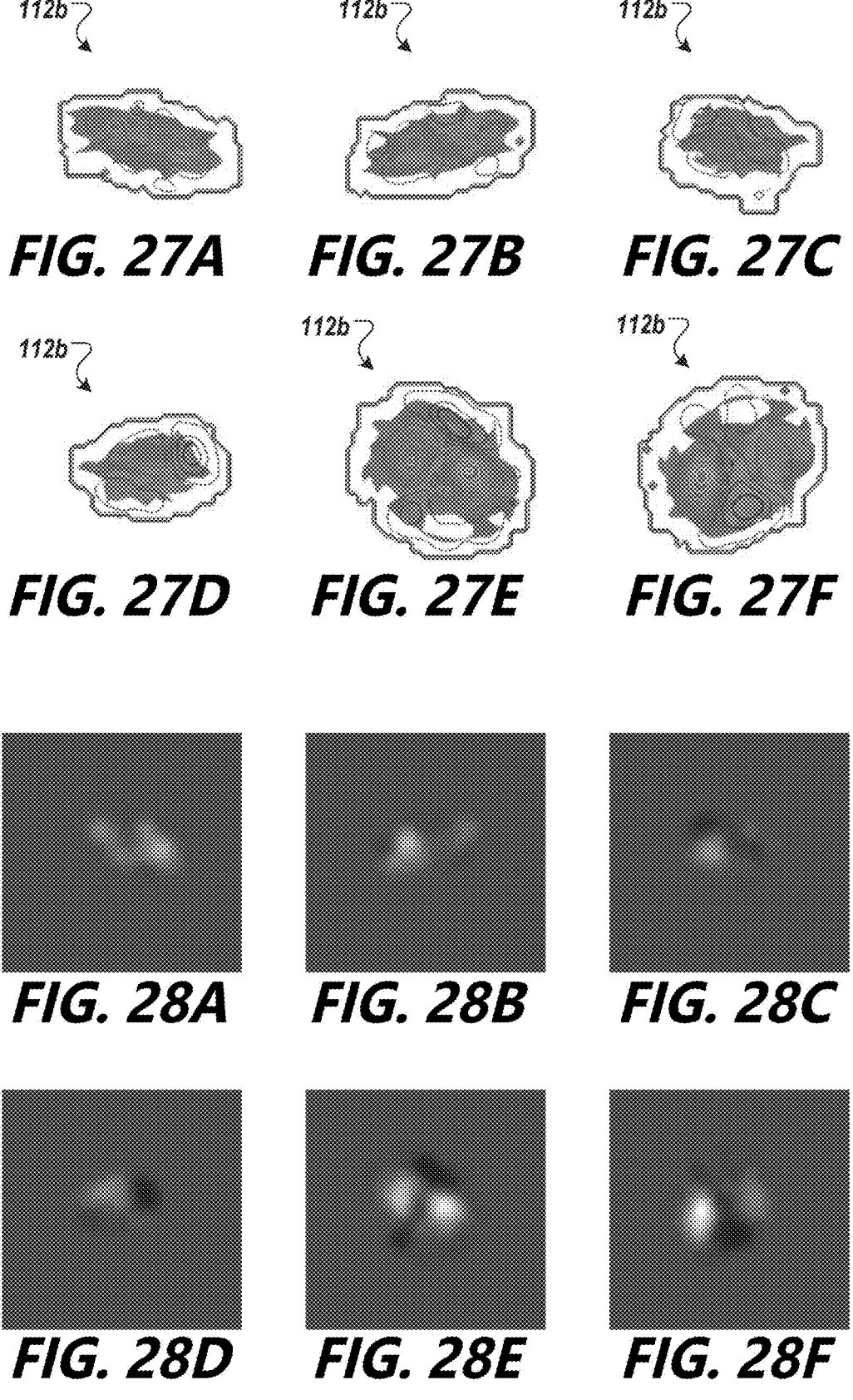
FIGS. 27A, 27B, 27C, 27D, 27E, and 27F show computed phase-space tomographic images derived from different views of a phase space volumetric object 112 (shown as 112b) associated with a subject diagnosed with significant coronary artery disease in accordance with an illustrative embodiment. The computed phase-space tomographic images are shown with contour data set and heat map data set generated from a neural network classifier applied to the computed phase-space tomographic images.
FIGS. 28A, 28B, 28C, 28D, 28E, and 28F show outputted classification of the tomographic images of FIGS. 27A-27F for presence and non-presence of significant coronary artery disease determined via a neural network classifier, in accordance with an illustrative embodiment.
Figure 29A:
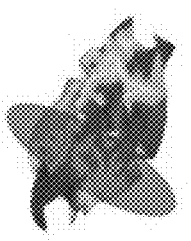
FIGS. 29A, 29B, 29C, 29D, 29E, and 29F show example two dimensional overlay superimposed over a three-dimensional volumetric object in accordance with an illustrative embodiment.
Figure 29B:
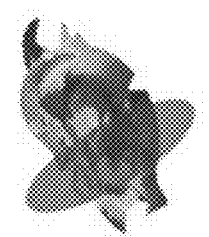
Figure 29C:
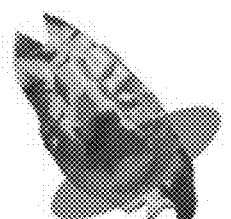
Figure 29D:
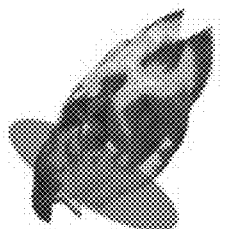
Figure 29E:
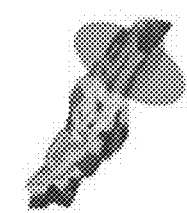
Figure 29F:
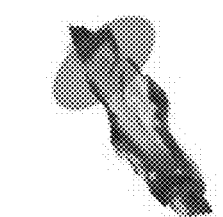
Figure 30A:
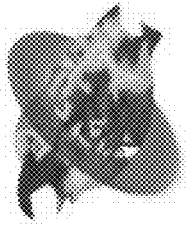
FIGS. 30A, 30B, 30C, 30D, 30E, and 30F show example three dimensional overlay superimposed over a three-dimensional volumetric object in accordance with an illustrative embodiment.
Figure 30B:
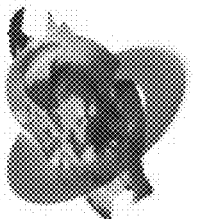
Figure 30C:
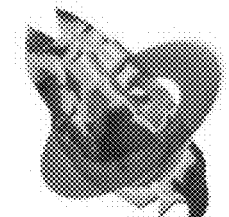
Figure 30D:
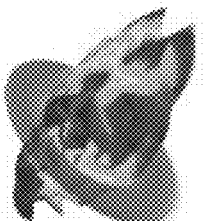
Figure 30E:
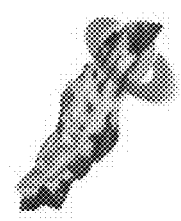
Figure 30F:
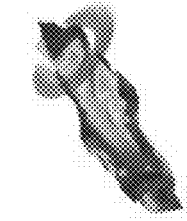

FIGS. 22A, 22B, 22C, 22D, 22E, and 22F show a set of computed phase-space tomographic images 2202, 2204, 2206, 2208, 2210, 2212 derived from six different views of the phase space volumetric object 112 (shown as 112a) associated with a healthy subject (i.e., a person assessed to not have significant coronary artery disease) in accordance with an illustrative embodiment. Specifically, FIG. 22A shows a right view (2202) of a phase space volumetric object 112a, which also corresponds to the x-axis of the phase space volumetric object 112a. FIG. 22B shows a left view (2204) of a phase space volumetric object 112a, which also corresponds to the other direction of the x-axis of the phase space volumetric object 112a. FIG. 22C shows a front view (2206) of a phase space volumetric object 112a, which also corresponds to the z-axis of the phase space volumetric object 112a. FIG. 22D shows a back view (2208) of a phase space volumetric object 112a, which also corresponds to the other direction along the z-axis of the phase space volumetric object 112a. FIG. 22E shows a top view (2210) of a phase space volumetric object 112a, which also corresponds to the y-axis of the phase space volumetric object 112a. FIG. 22F shows a bottom view (2212) of a phase space volumetric object 112a, which also corresponds to the other direction along the y-axis of the phase space volumetric object 112a. As shown, the images are created from 30 seconds of patient signal, and a total of five images were created per patient using non-overlapping sub-signals from the total 210 second available.

Neural Network Classification

The three-dimensional phase-space volumetric object or the computed phase-space tomographic images (e.g., 2202, 2204, 2206, 2208, 2210, 2212) can be directly evaluated by a trained neural network classifier to determine presence or non-presence of significant coronary artery disease. It is observed that a machine learned classifier can achieve a prediction having a ROC-AUC of 0.68 (0.49, 0.82). The characteristics of the development and test data sets used to train the machine learned classifier to produce this result is provided in table of FIG. 31.

In some embodiments, the neural network classifier may be a neural network trained on a set of grayscale tomographic images which are paired with coronary angiography results assessed for presence and non-presence of significant coronary artery disease. In some embodiments, a neural network-based nonlinear classifier is used. In some embodiments, the neural network-based non-linear classifier is configured to map individual pixels from the generated tomographic images to a binary CAD prediction. In some embodiments, the neural network's weights, which govern this mapping, is optimized using gradient descent techniques.

FIGS. 23A, 23B, 23C, 23D, 23E, and 23F show outputted classification of the tomographic images of FIGS. 22A-22F for presence and non-presence of significant coronary artery disease determined via a neural network classifier, in accordance with an illustrative embodiment. Each of the tomographic image of FIGS. 22A-22F are used as input to a neural network-based nonlinear classifier configured to map individual pixels from the tomographic images to a binary CAD prediction. Here, the classifier is configured to sweep a 4×4 moving window of white pixels (i.e., having a value of 1 in grayscale) over each respective image (e.g., 2202, 2204, 2206, 2208, 2210, 2212) with an output of the neural network being evaluated for each window position and its output being recorded. Because a given pixel in the resulting image is covered by more than one moving windows (i.e., in that the window is larger than a single pixel but moving one pixel at a time), each pixel in a heat map is determined as an average/mean of each of the applicable moving window. Here, contour plots are generated using the same data as the heat maps.

FIGS. 24A, 24B, 24C, 24D, 24E, and 24F show classification of the tomographic images of FIGS. 22A-22F overlaid with a contour data set and heat map associated with the classifier in accordance with an illustrative embodiment. As shown in the tomographic images, yellow and green contours (white on the heat maps) show areas contributing to a negative prediction of presence of significant coronary artery disease, while purple contours (black on the heat maps) show areas that are contributing to a positive prediction of presence of significant coronary artery disease.

In some embodiments, more than one phase space volumetric objects 112 are generated and evaluated from a single phase-gradient biophysical data set 108 acquired in a single acquisition session. For example, if a phase-gradient biophysical data set is acquired over about 210 seconds, and a set of phase space volumetric objects 112 is generated from about 30 seconds of data, then multiple phase space volumetric objects 112 (e.g., one to seven) could be generated and analyzed from non-overlapping portion of the phase-gradient biophysical data set.

In some embodiments, a neural network classifier containing a plurality of hidden neurons (e.g., 15 neurons or more) with leaky rectified linear activations is used. Dropout may be used between the hidden layer and the final output neuron, in some embodiments, to prevent overfitting. L1 and L2 regularization penalties may also be applied. Binary cross entropy may be used as a loss function, and optimization maybe performed using a gradient-based Adam algorithm.

Table 1 shows an example set of parameter values for the neural network, which were determined empirically. Other neural network types and configuration can be used.

TABLE 1

| Learning rate | $1e^{-5}$ |
|---|---|
| Alpha (for leaky rectified linear activations) | 0.3 |
| Dropout | 0.5 |
| L1/L2 penalty | 0.02 |
| Clipnorm | 1 |

FIGS. 25A, 25B, 25C, 25D, 25E, and 25F show only the contour data set and heat map data set of FIGS. 24A-24F in accordance with an illustrative embodiment.

FIGS. 26A, 26B, 26C, 26D, 26E, and 26F show computed phase-space tomographic images derived from different views of the phase space volumetric object 112 and overlaid with the contour data set and heat map data set generated from the neural network classifier of FIGS. 25A-25F in accordance with an illustrative embodiment.

FIGS. 27A, 27B, 27C, 27D, 27E, and 27F show computed phase-space tomographic images derived from different views of a phase space volumetric object 112 (shown as 112b) associated with a subject diagnosed with significant coronary artery disease in accordance with an illustrative embodiment. The computed phase-space tomographic images are shown with contour data set and heat map data set generated from a neural network classifier applied to the computed phase-space tomographic images.

FIGS. 28A, 28B, 28C, 28D, 28E, and 28F show outputted classification of the tomographic images of FIGS. 27A-27F for presence and non-presence of significant coronary artery disease determined via a neural network classifier, in accordance with an illustrative embodiment.

FIGS. 29A, 29B, 29C, 29D, 29E, and 29F show example two-dimensional overlays superimposed over a three-dimensional volumetric object in accordance with an illustrative embodiment. The two dimensional overlay are analogous to contours and are rendered in a three-dimensional space over the three-dimensional volumetric object to facilitate the visualization of the contour and heat map information over the three-dimensional volumetric object. Ovals and tori are not the only shapes possible for these overlays as other visualization elements can be used. FIGS. 30A, 30B, 30C, 30D, 30E, and 30F show example three dimensional overlay superimposed over a three-dimensional volumetric object in accordance with an illustrative embodiment. Different views of the three-dimensional volumetric objects superimposed with the 2D overlay or the 3D overlay can be generated as computed phase-space tomographic images.

FIGS. 32, 33, 34, 35, 36, 37, 38, and 39 show example graphical user interface for a clinician web portal, or a report derived therefrom, to view and assess cardiac phase space tomographic images, in accordance with an illustrative embodiment.

Figure 32:
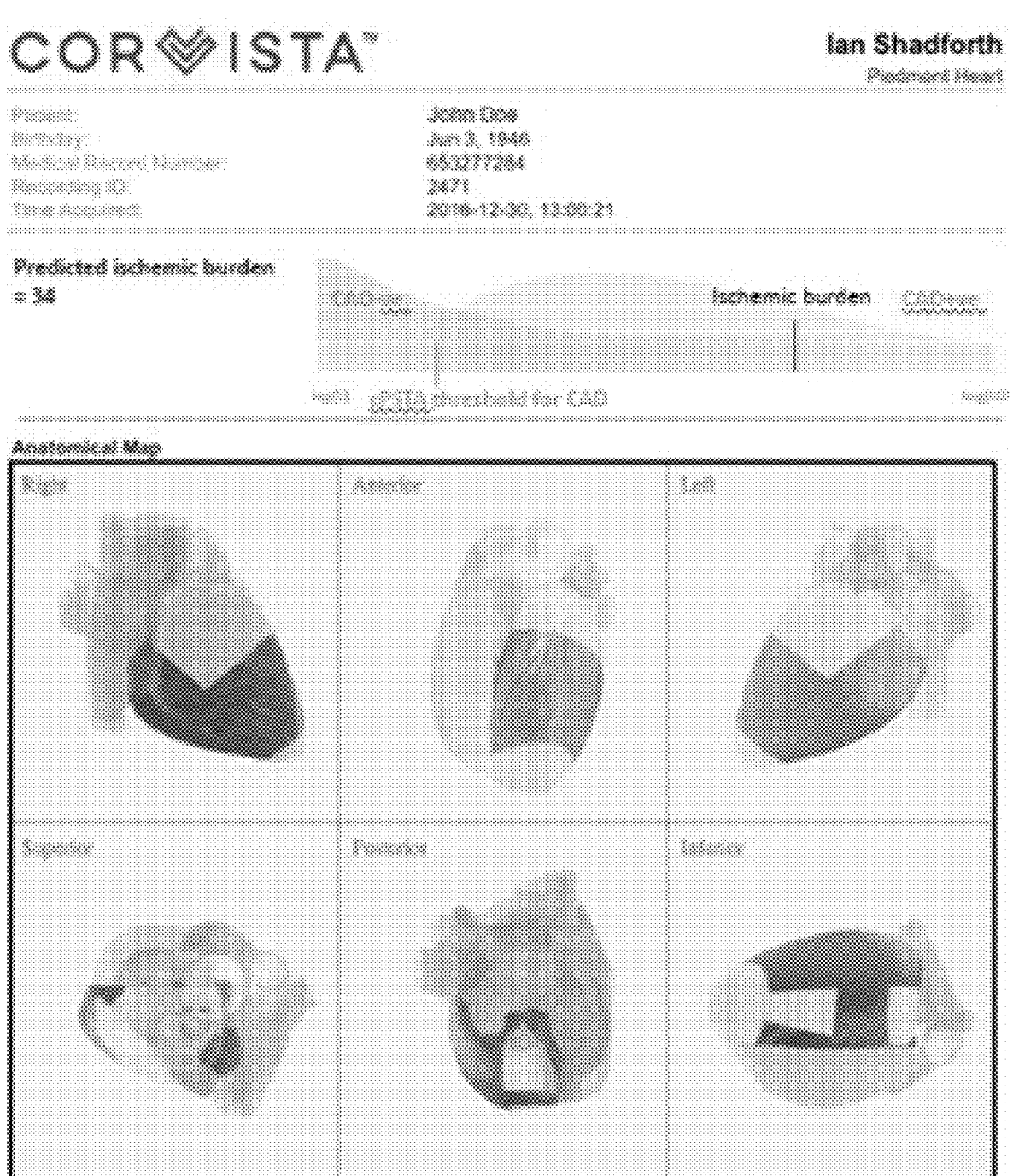

FIG. 32 shows a report with regions of myocardium at risk of significant coronary artery disease highlighted on a 17 segment anatomical heart map, in accordance with an illustrative embodiment. The subject here is diagnosed with significant coronary artery disease. In FIG. 32, the machine-assessed ischemic burden of the subject is shown. The areas designated with myocardium at risk may be derived from the assessment of presence or non-presence of significant coronary disease. Further description is provided in U.S. application Ser. No. 15/712,104, which is incorporated by reference herein in its entirety.

Figure 33:
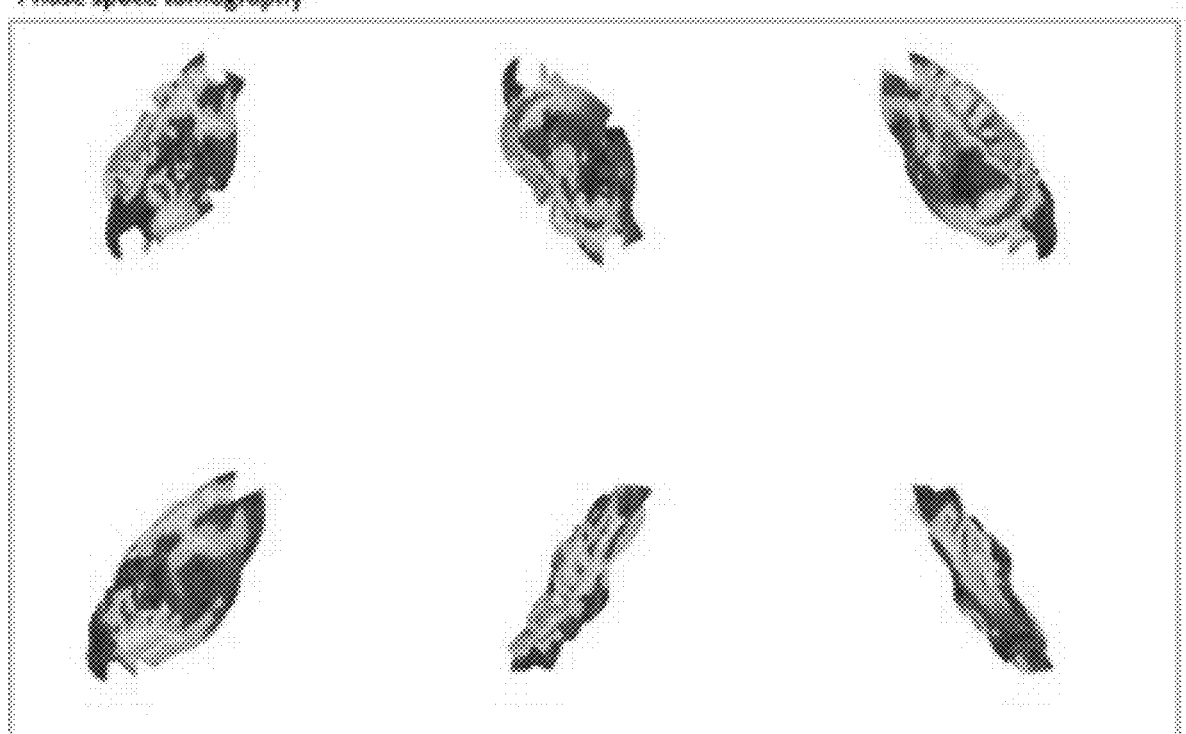

FIG. 33 shows example renderings of a three-dimensional volumetric object associated with the data set used to generate the report of FIG. 32, in accordance with an illustrative embodiment.

Figure 34:
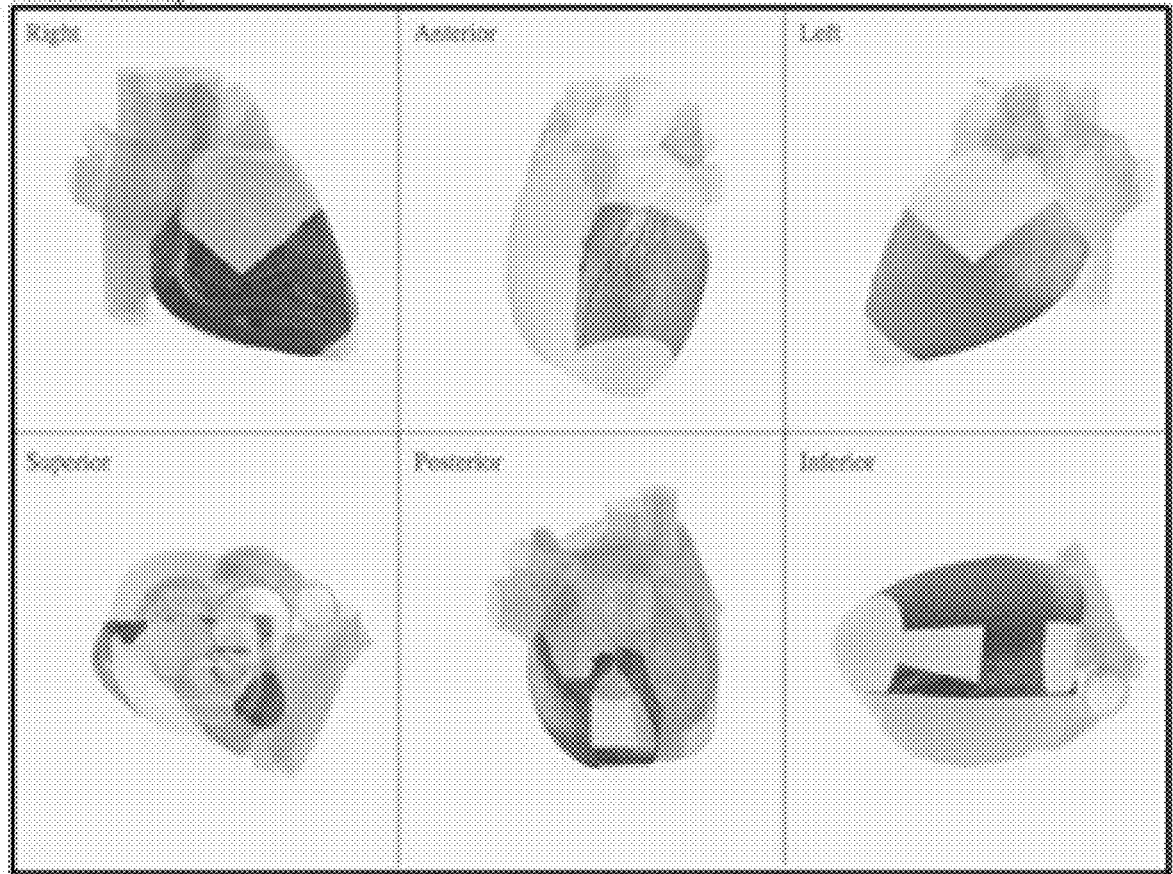

FIG. 34 shows another report with regions of myocardium at risk of significant coronary artery disease highlighted on a 17 segment anatomical heart map, in accordance with an illustrative embodiment. In FIG. 34, another presentation of the machine-assessed ischemic burden of the subject is shown.

Figure 35:
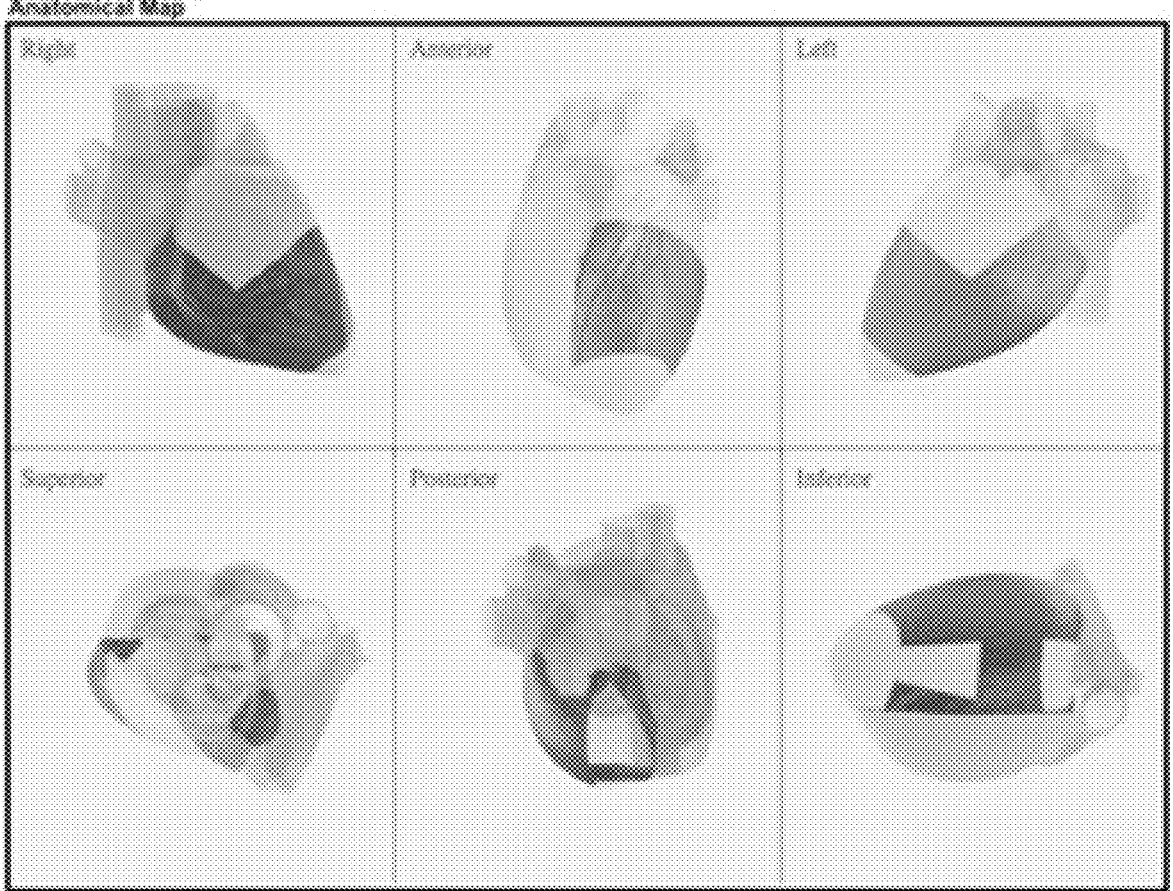

FIG. 35 shows another report with regions of myocardium at risk of significant coronary artery disease highlighted on a 17 segment anatomical heart map, in accordance with an illustrative embodiment. In FIG. 35, yet another presentation of the machine-assessed ischemic burden of the subject is shown.

FIG. 36 shows a report of an example renderings of a three-dimensional volumetric object associated with the data set used to generate the report of FIG. 32, in accordance with an illustrative embodiment. In FIG. 36, another presentation of the machine-assessed ischemic burden of the subject is shown in conjunction with the three-dimensional volumetric object.

Figure 37:
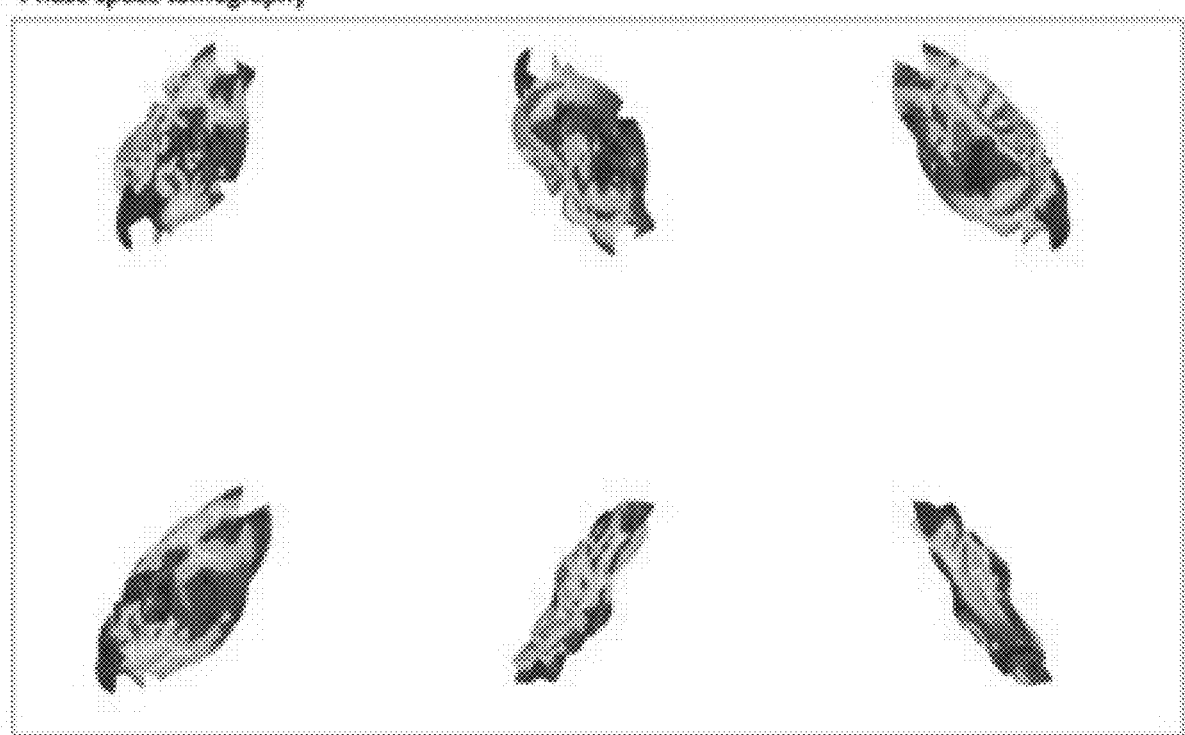

FIG. 37 shows a report of an example renderings of a three-dimensional volumetric object associated with the data set used to generate the report of FIG. 32, in accordance with an illustrative embodiment. In FIG. 37, yet another presentation of the machine-assessed ischemic burden of the subject is shown in conjunction with the three-dimensional volumetric object.

Figure 38:
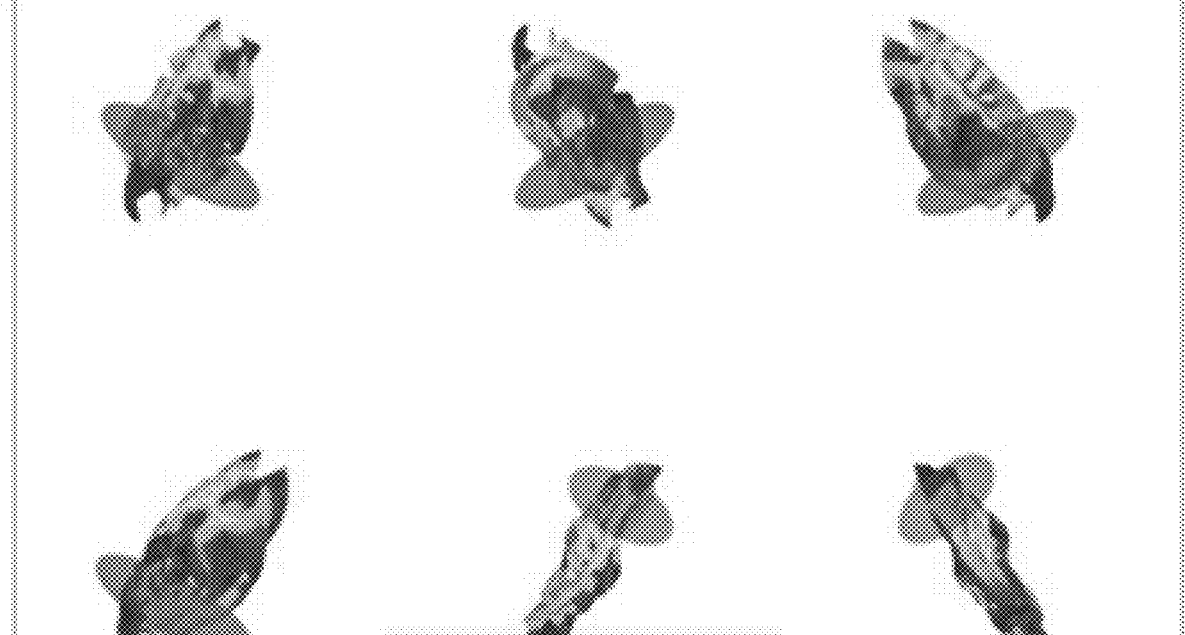

FIG. 38 shows a report of an example renderings of a three-dimensional volumetric object associated with the data set used to generate the report of FIG. 32, in accordance with an illustrative embodiment. In FIG. 38, machine-assessed two-dimensional contour overlays corresponding to risk are presented. An interpretative key is provided.

Figure 39:
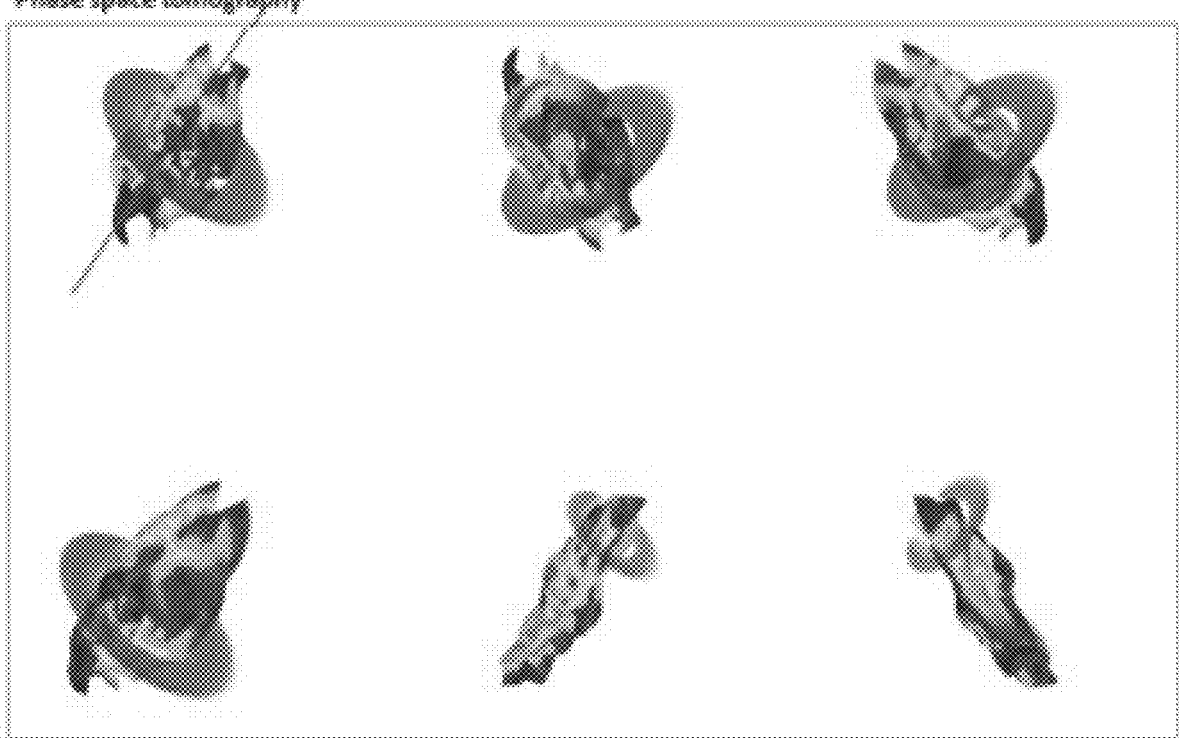

FIG. 39 shows a report of an example renderings of a three-dimensional volumetric object associated with the data set used to generate the report of FIG. 32, in accordance with an illustrative embodiment. In FIG. 39, machine-assessed three-dimensional contour overlays corresponding to risk are presented. An interpretative key is provided.

Biopotential-Based Measurement Equipment and Sensors

Referring to the embodiment of FIG. 1, system 100 includes biopotential-based measurement equipment 102 which, in some embodiments, is wide-band biopotential measuring equipment configured with bipotential sensing circuitries that, in the cardiography context, captures cardiac-related biopotential or electrophysiological signals of a living subject such as a human as wide-band cardiac phase gradient signals. Such equipment 102 may capture other biopotential or electrophysiological signals, such as, e.g., cerebral biopotential signals and other biophysical signals discussed herein.

As described in U.S. Publication No. 2017/0119272 and in U.S. Publication No. 2018/0249960, each of which is incorporated by reference herein in its entirety, the biopotential-based measurement equipment 102, in some embodiments, is configured to capture unfiltered electrophysiological signals such that the spectral component(s) of the signals are not altered. That is, all of the captured signal, if not a significant portion of the captured signal, includes, and does not exclude, components conventionally perceived/treated as and filtered out as noise (e.g., including those in the frequency range of greater than about 1 kHz). Further, the biopotential-based measurement equipment 102 of FIG. 1 can capture, convert, and even analyze the collected wide-band biopotential signals without any filtering (via, e.g., hardware circuitry and/or digital signal processing techniques, etc.) that otherwise can affect the phase linearity of the signal of interest in the wide-band biopotential signals.

In some embodiments, the biopotential-based measurement equipment 102 include wide-band equipment configured to capture one or more biosignals of a subject, such as biopotential signals, in microvolt or sub-microvolt resolutions that are at, or significantly below, the noise floor of conventional electrocardiographic and other biosignal acquisition instruments. In some embodiments, the wide-band biopotential measuring equipment is configured to acquire and record wide-band phase gradient signals (e.g., wide-band cardiac phase gradient signals, wide-band cerebral phase gradient signals) that are simultaneously sampled, in some embodiments, having a temporal skew or "lag" of less than about 1 µs, and in other embodiments, having a temporal skew or lag of not more than about 10 femtoseconds. Notably, the exemplified system minimizes non-linear distortions (e.g., those that can be introduced via certain filters) in the acquired wide-band phase gradient signal so as to not affect the information therein.

Phase Space Transformation and Analysis

As described in U.S. patent application Ser. No. 15/633,330, a phase space analysis system is configured to generate a phase space map to be used to non-invasively measure myocardial ischemia based on features extracted from such phase space map.

Figure 7:
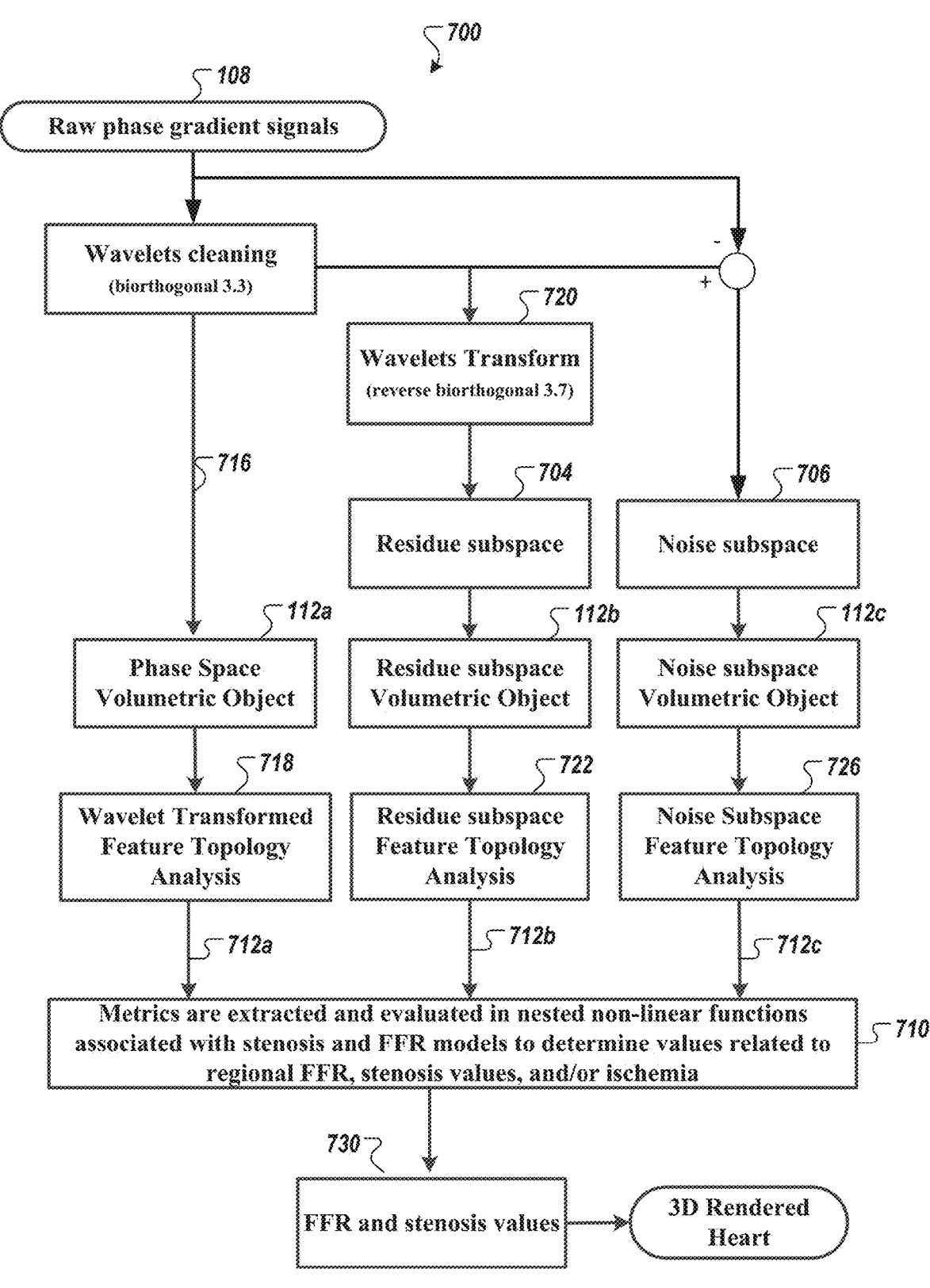
FIG. 7 is a diagram of an exemplary method of processing the phase-gradient biophysical data set in accordance with an illustrative embodiment.

FIG. 7 is a diagram of an exemplary method 700 of processing the phase-gradient biophysical data set 108 in accordance with an illustrative embodiment. The method 700 includes collecting and phase-gradient biophysical data set 108 to generate, via phase space analysis techniques, a phase space dataset (shown as input data 716, "residue subspace" dataset 704 and "noise subspace" dataset 706). The characteristics of the phase space data set (704, 706) and input data set (716) may be extracted, in a feature extraction operation (e.g., analysis steps 718, 722, 726) to determine geometric and dynamic properties of the data set. These subspaces may include, but are not limited to, complex subharmonic frequency (CSF) trajectory, quasi-periodic and chaotic subspaces, low/high energy subspaces, and fractional derivatives of the low/high energy subspaces. These subspaces are exemplars of the family of subspaces that characterize the dynamics of the system, whether pathological or normal. In some embodiments, the extracted metrics are generated from the phase space volumetric object 112 (shown as 112a, 112b, and 112c) and generated from one or more of the phase space data sets (704, 706) and/or the input data set (716).

As shown in FIG. 7, one or more of the phase space data sets (704, 706) and/or the input data set (716), in some embodiments, are evaluated via fractional derivative operations to generate point cloud data set to which faces are generated via triangulation. In some embodiments, one or more color map data sets are generated for the determined vertex data set. Metrics (e.g., extracted metrics 712a, 712b, 712c) are assessed including a volume metric (e.g., alpha hull volume), a number of distinct bodies (e.g., distinct volumes), and/or a maximal color variation (e.g., color gradient) of the generated phase space volumetric object 112.

The extracted metrics (712a, 712b, 712c) can be subsequently evaluated via, e.g., nested non-linear functions 710 (associated with stenosis and/or FFR models) to estimate values 730 for a given subject related to, e.g., regional FFR, the presence and/or degree of a stenosis, ischemia, or presence or non-presence of significant coronary artery disease, etc. In some embodiments, the values associated with regional FFR and the presence and/or degree of a stenosis and ischemia are then mapped to point-cloud representation of a three-dimensional model of the heart.

Analysis using phase space analysis techniques as described herein can facilitate understanding of different bioelectric structures within mammalian tissue, including but not limited to tissue in or associated with organs such as the brain or the heart. For example, various types of cardiac tissue, particularly but not necessarily when such tissue is/are damaged or unhealthy, may exhibit different conduction characteristics, such as can be exhibited by differences in tissue impedance. Indeed, these techniques can be used to understand spectral and non-spectral conduction delays and bends in the trajectory of the phase space orbit as it propagates through the heart. These small changes in trajectory can further be normalized and quantified on a beat-to-beat basis and corrected for abnormal or poor lead placement. The normalized phase space integrals can also be visualized on, or mapped to, a geometric mesh (e.g., a model of the heart) using a genetic algorithm. In some embodiments, these phase space integrals are mapped to myocardial segments in the heart. In some embodiments, these mapped myocardial segments can correspond to the 17-segments of the left ventricular model of the heart. Other number of myocardial segments may be used.

Referring still to FIG. 7, three distinct phase space analyses are performed to generate sets of metrics and variables (shown as steps 712a, 712b, and 712c). The metrics and variable are then used in the non-linear functions (e.g., as shown in step 710) to generate regional FFR estimation values, regional stenosis values, and regional ischemia values 730. Table 2 is an example output matrix of these values 122.

TABLE 2

| Segment | Vessel | FFR | Stenosis | Ischemia |
|---|---|---|---|---|
| 1 | Left Main Artery (LMA) | 0.90 | 0.50 | 0.20 |
| 2 | Proximal Left Circumflex Artery (Prox LCX) | 0.85 | 0.60 | 0.30 |
| 3 | Mid - Left Circumflex Artery (Mid LCX) | 0.93 | 0.35 | 0.15 |
| 4 | Distal Left Circumflex Artery (Dist LCX) | 1.00 | 0.00 | 0.00 |
| 5 | Left Posterior Atrioventricular (LPAV) | 1.00 | 0.00 | 0.00 |
| 6 | First Obtuse Marginal (OM1) | 0.60 | 0.95 | 0.72 |
| 7 | Second Obtuse Marginal (OM2) | 1.00 | 0.00 | 0.00 |
| 8 | Third Obtuse Marginal (OM3) | 1.00 | 0.00 | 0.00 |
| 9 | Proximal Left Anterior Descending Artery (Prox LAD) | 1.00 | 0.00 | 0.00 |
| 10 | Mid Left Anterior Descending Artery (Mid LAD) | 1.00 | 0.00 | 0.00 |
| 11 | Distal Left Anterior Descending Artery (Dist LAD) | 0.70 | 0.80 | 0.63 |
| 12 | LAD D1 | 0.00 | 0.00 | 0.75 |
| 13 | LAD D2 | 0.00 | 0.00 | 0.00 |
| 14 | Proximal Right Coronary Artery (Prox RCA) | 0.00 | 0.00 | 0.00 |
| 15 | Mid Right Coronary Artery (Mid RCA) | 0.00 | 0.00 | 0.00 |
| 16 | Distal Right Coronary Artery (Dist RCA) | 0.00 | 0.00 | 0.18 |
| 17 | Acute Marginal Brach Right of the Posterior Descending Artery (AcM R PDA) | 0.00 | 0.00 | 0.00 |

As shown, Table 2 includes numerical values for a fractional flow reserve (FFR) parameter, an estimated stenosis parameter, and an estimated ischemia parameter for a plurality of (in this case, 17) segments corresponding to major vessels of a human heart. In some embodiments, matrix of the value 730 includes numerical values of a fractional flow reserve (FFR) parameter, an estimated stenosis parameter, and an estimated ischemia parameter for a standardized myocardial segment map having 17 segments of the heart including the left main artery (LMA), a proximal left circumflex artery (Prox LCX), a mid-left circumflex artery (mid LCX), a distal left circumflex artery (Dist LCX), a LPAV, a first obtuse marginal (OM1), a second obtuse marginal (OM2), a third obtuse marginal (OM3), a proximal left anterior descending artery (Prox LAD), a mid left anterior descending artery (Mid LAD), a distal left anterior descending artery (Dist LAD), LAD D1, LAD D2, a proximal right coronary artery (Prox RCA), a mid-right coronary artery (Mid RCA), a distal right coronary artery (Dist RCA), and an acute marginal branch right of the posterior descending artery (AcM R PDA).

In Table 2, the parameter values for myocardial ischemia estimation, stenosis identification, and/or fractional flow reserve estimation are shown in a range of 0 to 1. Other scaling or ranges may be used, such as other non-numerical values to indicate a relative degree of the parameter of interest compared to a nominal standard.

Tables 3-6 show example non-linear functions used to generate FFR estimations for several segments corresponding to major vessels in the heart. In Table 3, an example function to determine a FFR estimation for the left main artery ("FFR_LEFTMAIN") is provided.

TABLE 3

FFR_LEFTMAIN = 0.128467341682411*noisevectorRz*atan2(Alpharatio, DensityV4)

As shown in Table 3, the FFR estimation for the left main artery is determined based on extracted metrics and/or variables such as a Z-component parameter associated with the noise subspace ("noisevectorRz"), a Alphahull ratio parameter ("Alpharatio"), and a signal density cloud volume 4 ("DensityV4").

In Table 4, an example function to determine a FFR estimation for the mid right coronary artery ("FFR_MIDRCA") is provided.

TABLE 4

FFR_MIDRCA = 0.0212870065789474*noisevectorRy*Alpharatio*DensityV3

As shown in Table 4, the FFR estimation for the mid right coronary artery is determined based on extracted metrics and/or variables such as a Y-component parameter associated with the noise subspace ("noisevectorRy"), the Alphahull ratio parameter ("Alpharatio"), and a signal density cloud volume 3 ("DensityV3").

In Table 5, an example function to determine a FFR estimation for the mid left artery descending ("FFR_MIDLAD") is provided.

TABLE 5

FFR_MIDLAD = atan2(AspectRatio3, residueLevelMean)

As shown in Table 5, the FFR estimation for the mid left artery descending is determined based on extracted metrics and/or variables such as a ratio of volume to surface area for cloud cluster 3 ("AspectRatio3") and a wavelet residue mean XYZ ("residueLevelMean").

In Table 6, an example function to determine a FFR estimation for the proximal left circumflex artery ("FFR_PROXLCX") is provided.

TABLE 6

FFR_PROXLCX = 0.408884581034257*atan2(residueLevelVolume+vectorcloud6, DensityV4)

As shown in Table 6, the FFR estimation for the proximal left circumflex artery is determined based on extracted metrics and/or variables such as a wavelet residue volume XYZ ("residueLevelVolume"), vector cloud 6 volume ("vectorcloud6"), and a signal density cloud volume 4 ("DensityV4").

The output of the phase space analysis is then evaluated using machine learning analysis to assess parameters associated with a presence and/or degree of a disease or physiological characteristic (such as, e.g., in the cardiovascular context, regional arterial flow characteristics). In some embodiments, the machine learning analysis may use a library of quantified FFR, stenosis, and ischemia data (e.g., data acquired from a study of coronary arterial disease) in the assessment of the obtained wide-band cardiac gradient signal data.

The output of a processor performing the analysis may then be transmitted to a graphical user interface, such as, e.g., a touchscreen or other monitor, for visualization. The graphical user interface, in some embodiments, is included in a display unit configured to display values of any number of parameters discussed herein and elsewhere. In some embodiments, the graphical user interface displays these data in formats such as, e.g., a three-dimensional phase space plot representation of the biopotential signal data and virtual biopotential signal data. In other embodiments, the data output of the processor is or may also be simultaneously or sequentially transmitted to one or more non-graphical user interfaces (e.g., printout, command-line or text-only user interface), directly to a database or memory device, processor, firmware, hardware and/or software for, e.g., later retrieval and/or additional analysis, other machines that may include non-graphical user interfaces for the display of such data, or combinations thereof. Any device, machine, or medium capable of receiving data and being interpreted by a human or machine or used for further processing is contemplated and within the scope of the present disclosure.

A visualization engine may receive the determined arterial flow characteristics (such as FFR or stenosis values) and renders the characteristics onto a three dimensional visualization output. In some embodiments, the visualization engine provides, in a graphical user interface (GUI), a system-level view of all of the arterial flow characteristics and their interactions. In some embodiments, the GUI presents the cascading effects of upstream modifications to the arterial flow upon the downstream circulation. Further description of an example visualization engine is provided in U.S. Publication No. 2018/0078146, title "Method and System for Visualization of Heart Tissue at Risk", which is incorporated by reference herein in its entirety.

Further examples of phase space and various processing that may be used with the exemplified method and system are described in: U.S. Pat. No. 9,289,150, title "Non-invasive Method and System for Characterizing Cardiovascular Systems"; U.S. Pat. No. 9,655,536, title "Non-invasive Method and System for Characterizing Cardiovascular Systems"; U.S. Pat. No. 9,968,275, title "Non-invasive Method and System for Characterizing Cardiovascular Systems"; U.S. Pat. No. 8,923,958, title "System and Method for Evaluating an Electrophysiological Signal"; U.S. Pat. No. 9,408,543, title "Non-invasive Method and System for Characterizing Cardiovascular Systems and All-Cause Mortality and Sudden Cardiac Death Risk"; U.S. Pat. No. 9,955,883, title "Non-invasive Method and System for Characterizing Cardiovascular Systems and All-Cause Mortality and Sudden Cardiac Death Risk"; U.S. Pat. No. 9,737,229, title "Noninvasive Electrocardiographic Method for Estimating Mammalian Cardiac Chamber Size and Mechanical Function"; U.S. Pat. No. 10,039,468, title "Noninvasive Electrocardiographic Method for Estimating Mammalian Cardiac Chamber Size and Mechanical Function"; U.S. Pat. No. 9,597,021, title "Noninvasive Method for Estimating Glucose, Glycosylated Hemoglobin and Other Blood Constituents"; U.S. Pat. No. 9,968,265, title "Method and System for Characterizing Cardiovascular Systems From Single Channel Data"; U.S. Pat. No. 9,910,964, title "Methods and Systems Using Mathematical Analysis and Machine Learning to Diagnose Disease"; U.S. Publication No. 2017/0119272, title "Method and Apparatus for Wide-Band Phase Gradient Signal Acquisition"; U.S. Publication No. 2018/0000371, title "Non-invasive Method and System for Measuring Myocardial Ischemia, Stenosis Identification, Localization and Fractional Flow Reserve Estimation"; U.S. Publication No. 2018/0078146, title "Method and System for Visualization of Heart Tissue at Risk"; U.S. Publication No. 2018/0249960, title "Method and System for Wide-band Phase Gradient Signal Acquisition"; U.S. application Ser. No. 16/232,801, filed concurrently herewith (and claims priority to U.S. Provisional Appl. No. 62/611,826), title "Method and System to Assess Disease Using Phase Space Volumetric Objects"; U.S. application Ser. No. 16/165,641, title "Methods and Systems of De-Noising Magnetic-Field Based Sensor Data of Electrophysiological Signals"; U.S. application Ser. No. 16/232,586, filed concurrently herewith (and claims priority to U.S. Provisional Appl. No. 62/612, 130), title "Method and System to Assess Disease Using Phase Space Tomography and Machine Learning"; U.S. application Ser. No. 15/653,433, title "Discovering Novel Features to Use in Machine Learning Techniques, such as Machine Learning Techniques for Diagnosing Medical Conditions"; U.S. application Ser. No. 15/653,431, title "Discovering Genomes to Use in Machine Learning Techniques", each of which is incorporated by reference herein in its entirety.

Example Computing Device

Figure 40:
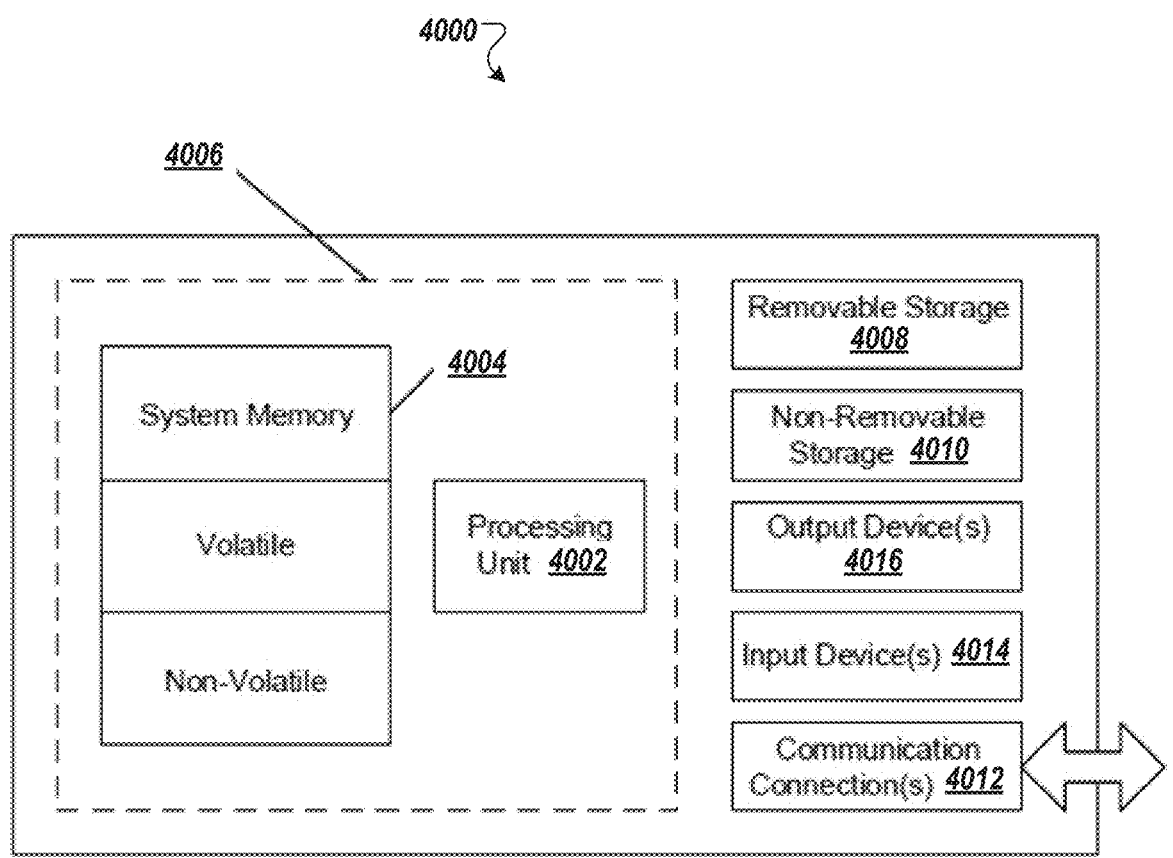
FIG. 40 shows an exemplary computing environment in which example embodiments of the assessment system 110 and aspects thereof may be implemented.

FIG. 40 shows an exemplary computing environment in which example embodiments and aspects may be implemented.

The computing device environment is only one example of a suitable computing environment and is not intended to suggest any limitation as to the scope of use or functionality.

Numerous other general-purpose or special purpose computing devices environments or configurations may be used. Examples of well-known computing devices, environments, and/or configurations that may be suitable for use include, but are not limited to, personal computers, server computers, handheld or laptop devices, multiprocessor systems, microprocessor-based systems, network personal computers (PCs), minicomputers, mainframe computers, embedded systems, distributed computing environments that include any of the above systems or devices, and the like.

Computer-executable instructions, such as program modules, being executed by a computer may be used. Generally, program modules include routines, programs, objects, components, data structures, etc. that perform particular tasks or implement particular abstract data types. Distributed computing environments may be used where tasks are performed by remote processing devices that are linked through a communications network or other data transmission medium. In a distributed computing environment, program modules and other data may be located in both local and remote computer storage media including memory storage devices.

With reference to FIG. 40, an exemplary system for implementing aspects described herein includes a computing device, such as computing device 4000. In its most basic configuration, computing device 4000 typically includes at least one processing unit 4002 and memory 4004. Depending on the exact configuration and type of computing device, memory 4004 may be volatile (such as random access memory (RAM)), non-volatile (such as read-only memory (ROM), flash memory, etc.), or some combination of the two. This most basic configuration is illustrated in FIG. 40 by dashed line 4006.

Computing device 4000 may have additional features/ functionality. For example, computing device 4000 may include additional storage (removable and/or non-removable) including, but not limited to, magnetic or optical disks or tape. Such additional storage is illustrated in FIG. 40 by removable storage 4008 and non-removable storage 4010.

Computing device 4000 typically includes a variety of computer readable media. Computer readable media can be any available media that can be accessed by the device 4000 and includes both volatile and non-volatile media, removable and non-removable media.

Computer storage media include volatile and non-volatile, and removable and non-removable media implemented in any method or technology for storage of information such as computer readable instructions, data structures, program modules or other data. Memory 4004, removable storage 4008, and non-removable storage 4010 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information, and which can be accessed by computing device 4000. Any such computer storage media may be part of computing device 4000.

Computing device 4000 may contain communication connection(s) 4012 that allow the device to communicate with other devices. Computing device 4000 may also have input device(s) 4014 such as a keyboard, mouse, pen, voice input device, touch input device, etc, singularly or in combination. Output device(s) 4016 such as a display, speakers, printer, vibratory mechanisms, etc. may also be included singularly or in combination. All these devices are well known in the art and need not be discussed at length here.

It should be understood that the various techniques described herein may be implemented in connection with hardware components or software components or, where appropriate, with a combination of both. Illustrative types of hardware components that can be used include Graphical Processing Units (GPUs), Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. The methods and apparatus of the presently disclosed subject matter, or certain aspects or portions thereof, may take the form of program code (i.e., instructions) embodied in tangible media, such as floppy diskettes, CD-ROMs, hard drives, or any other machine-readable storage medium where, when the program code is loaded into and executed by a machine, such as a computer, the machine becomes an apparatus for practicing the presently disclosed subject matter.

Although exemplary implementations may refer to utilizing aspects of the presently disclosed subject matter in the context of one or more stand-alone computer systems, the subject matter is not so limited, but rather may be implemented in connection with any computing environment, such as a network or distributed computing environment. Still further, aspects of the presently disclosed subject matter may be implemented in or across a plurality of processing chips or devices, and storage may similarly be effected across a plurality of devices. Such devices might include personal computers, network servers, handheld devices, and wearable devices, for example.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

While the methods and systems have been described in connection with certain embodiments and specific examples, it is not intended that the scope be limited to the particular embodiments set forth, as the embodiments herein are intended in all respects to be illustrative rather than restrictive.

The methods, systems and processes described herein may be used generate stenosis and FFR outputs for use in connection with procedures such as the placement of vascular stents within a vessel such as an artery of a living (e.g., human) subject, and other interventional and surgical system or processes. In one embodiment, the methods, systems and processes described herein can be configured to use the FFR/stenosis outputs to determine and/or modify, intra operation, a number of stents to be placed in a living (e.g., human), including their optimal location of deployment within a given vessel, among others.

Examples of other biophysical signals that may be analyzed in whole, or in part, using the exemplary methods and systems include, but are not limited to, an electrocardiogram (ECG) data set, an electroencephalogram (EEG) data set, a gamma synchrony signal data set; a respiratory function signal data set; a pulse oximetry signal data set; a perfusion data signal data set; a quasi-periodic biological signal data set; a fetal ECG data set; a blood pressure signal; a cardiac magnetic field data set, and a heart rate signal data set.

The exemplary analysis can be used in the diagnosis and treatment of cardiac-related pathologies and conditions and/or neurological-related pathologies and conditions, such assessment can be applied to the diagnosis and treatment (including, surgical, minimally invasive, and/or pharmacologic treatment) of any pathologies or conditions in which a biophysical signal is involved in any relevant system of a living body. One example in the cardiac context is the diagnosis of CAD and its treatment by any number of therapies, alone or in combination, such as the placement of a stent in a coronary artery, performance of an atherectomy, angioplasty, prescription of drug therapy, and/or the prescription of exercise, nutritional and other lifestyle changes, etc. Other cardiac-related pathologies or conditions that may be diagnosed include, e.g., arrhythmia, congestive heart failure, valve failure, pulmonary hypertension (e.g., pulmonary arterial hypertension, pulmonary hypertension due to left heart disease, pulmonary hypertension due to lung disease, pulmonary hypertension due to chronic blood clots, and pulmonary hypertension due to other disease such as blood or other disorders), as well as other cardiac-related pathologies, conditions and/or diseases. Non-limiting examples of neurological-related diseases, pathologies or conditions that may be diagnosed include, e.g., epilepsy, schizophrenia, Parkinson's Disease, Alzheimer's Disease (and all other forms of dementia), autism spectrum (including Asperger syndrome), attention deficit hyperactivity disorder, Huntington's Disease, muscular dystrophy, depression, bipolar disorder, brain/spinal cord tumors (malignant and benign), movement disorders, cognitive impairment, speech impairment, various psychoses, brain/spinal cord/ nerve injury, chronic traumatic encephalopathy, cluster headaches, migraine headaches, neuropathy (in its various forms, including peripheral neuropathy), phantom limb/ pain, chronic fatigue syndrome, acute and/or chronic pain (including back pain, failed back surgery syndrome, etc.), dyskinesia, anxiety disorders, conditions caused by infections or foreign agents (e.g., Lyme disease, encephalitis, rabies), narcolepsy and other sleep disorders, post-traumatic stress disorder, neurological conditions/effects related to stroke, aneurysms, hemorrhagic injury, etc., tinnitus and other hearing-related diseases/conditions and vision-related diseases/conditions.

What is claimed is:

1. A method for non-invasively assessing presence or non-presence of significant coronary artery disease, the method comprising:

obtaining, by one or more processors, acquired data from a measurement of one or more biophysical signals of a subject, wherein the acquired data are derived from measurements acquired via noninvasive equipment configured to measure properties of a heart;

generating, by one or more processors, a plurality of low-energy subspace parameters from the acquired data;

generating, by the one or more processors, a three-dimensional model defining a volume and a surface based on a residual analysis of the low-energy subspace parameters generated from the acquired data;

generating, by the one or more processors, a set of two-dimensional images derived from the three-dimensional model, including a first and a second two-dimensional image, wherein each two-dimensional image of the set of two-dimensional images is a different view of the three-dimensional model, wherein each two-dimensional image of the set of two-dimensional images synthesizes and displays the electrical and functional characteristics of the heart; and determining an output indicating the presence or non-presence of significant coronary artery disease, using an output of a trained neural network, wherein the trained neural network comprises a neural network trained using two-dimensional images of the set of two-dimensional images that are paired with coronary angiography results assessed for the presence or non-presence of significant coronary artery disease, wherein the output of the trained neural network is subsequently used for an assessment of presence and/or non-presence of significant coronary artery disease.

2. The method of claim 1, wherein each of the two-dimensional images is generated by:

determining, by the one or more processors, a machine-trained assessment of presence and/or non-presence of significant coronary artery disease using a trained neural network-based nonlinear classifier.

3. The method of claim 1, comprising:

generating a contour data set for each two-dimensional image of the set of two-dimensional images, wherein the contour data in each contour data set are presented for the assessment of presence and/or non-presence of significant coronary artery disease.

4. The method of claim 3, wherein each two-dimensional image comprises a plurality of pixels, and further wherein the contour data set is generated by:

sweeping, via the one or more processors, a moving window associated with the trained neural network-based nonlinear classifier on a pixel-by-pixel basis over, at least a portion of, a given two-dimensional image; and combining, for a given pixel of the two-dimensional image, outputs of the swept moving window.

5. The method of claim 4, comprising:

presenting, via the display of the remote computing system, the generated contour data set and a corresponding two-dimensional image used to generate the contour data set, wherein the generated contour data set is rendered as an overlay over the corresponding two-dimensional image.

6. The method of claim 4, wherein the generated contour data set comprises color map data, the method further includes the step of presenting, via a display of the remote computing system, the set of two-dimensional images in conjunction with the generated contour data set.

7. The method of claim 1, wherein vertices and faces of the generated three-dimensional model comprise color data, and wherein the step of generating the two-dimensional images comprising converting the generated three-dimensional model to greyscale.

8. The method of claim 1, wherein the two-dimensional images are generated by:

generating a plurality of images corresponding to a plurality of orientations of the generated three-dimensional model, wherein the images are generated at a first image resolution; and converting the plurality of images to a second image resolution, wherein the second image resolution is different from the first image resolution.

9. The method of claim 1, further comprising:

determining, by the one or more processors, one or more coronary physiological parameters of the subject selected from the group consisting of a fractional flow reserve estimation, a stenosis value, and a myocardial ischemia estimation, based on the generated three-dimensional model; and causing, by the one or more processors, output of the one or more coronary physiological parameters.

10. The method of claim 1, wherein the generated three-dimensional model comprises a three-dimensional object defined by a plurality of faces and a plurality of vertices.

11. The method of claim 10, wherein the plurality of vertices are generated as a point cloud in 3D space, wherein each point in the point cloud has a value associated with a fractional order of a fractional subspace derivative operation of one or more of the plurality of low-energy subspace parameters.

12. The method of claim 11, wherein the fractional order is a rational number or an irrational number associated with one or more linear and/or non-linear dynamic response of the heart.

13. The method of claim 11, wherein the fractional order of the fractional subspace derivative operation is predetermined.

14. The method of claim 10, wherein each of the plurality of vertices or each of the plurality of faces comprises one or more attribute parameters.

15. The method of claim 14, wherein the one or more attribute parameters comprise color attribute parameters, where at least one of the one or more color attribute parameters is associated with a variance of a modeled channel signal generated from a model-derived construction of the acquired data subtracted from a baseline-removed raw channel of the acquired data.

16. The method of claim 14, wherein at least one of the one or more color attribute parameters is a triangular interpolation among bounding vertex attribute parameters.

17. The method of claim 1, wherein the three-dimensional model comprises a plurality of vertices and a plurality of faces, and further wherein the plurality of faces are generated from a triangulation operation of the plurality of vertices, wherein the plurality of faces are generated from a triangulation operation, the triangulation operation being selected from the group consisting of Delaunay triangulation, Mesh generation, Alpha Hull triangulation, and Convex Hull triangulation.

18. A system for non-invasively assessing presence or non-presence of significant coronary artery disease, the system comprising:
    one or more processors; and
    a non-transitory computer-readable medium storing computer-executable instructions that when executed by the one or more processors cause the system to:
        obtain acquired data from a measurement of one or more biophysical signals of a subject, wherein the acquired data are derived from measurements acquired via noninvasive equipment configured to measure properties of a heart;
        generate a plurality of low-energy subspace parameters from the acquired data;
        generate a three-dimensional model defining a volume and a surface based on a residual analysis of the low-energy subspace parameters generated from the acquired data;
        generate a set of two-dimensional images derived from the three-dimensional model, including a first and a second two-dimensional image, wherein each two-dimensional image of the set of two-dimensional images is a different view of the three-dimensional model, wherein each two-dimensional image of the set of two-dimensional images synthesizes and displays the electrical and functional characteristics of the heart; and determine an output indicating the presence or non-presence of significant coronary artery disease, using an output of a trained neural network, wherein the trained neural network comprises a neural network trained using two-dimensional images of the set of two-dimensional images that are paired with coronary angiography results assessed for the presence or non-presence of significant coronary artery disease, wherein the output of the trained neural network is subsequently used for an assessment of presence and/or non-presence of significant coronary artery disease.

19. A non-transitory computer-readable medium storing computer-executable instructions that when executed by one or more processors cause a system to:
    obtain acquired data from a measurement of one or more biophysical signals of a subject, wherein the acquired data are derived from measurements acquired via non-invasive equipment configured to measure properties of a heart;
    generate a plurality of low-energy subspace parameters from the acquired data;
    generate a three-dimensional model defining a volume and a surface based on a residual analysis of the low-energy subspace parameters generated from the acquired data;
    generate a set of two-dimensional images derived from the three-dimensional model, including a first and a second two-dimensional image, wherein each two-dimensional image of the set of two-dimensional images is a different view of the three-dimensional model, wherein each two-dimensional image of the set of two-dimensional images synthesizes and displays the electrical and functional characteristics of the heart; and
    determine an output indicating the presence or non-presence of significant coronary artery disease, using an output of a trained neural network, wherein the trained neural network comprises a neural network trained using two-dimensional images of the set of two-dimensional images that are paired with coronary angiography results assessed for the presence or non-presence of significant coronary artery disease, wherein the output of the trained neural network is subsequently used for an assessment of presence and/or non-presence of significant coronary artery disease.

20. The method of claim 1, wherein the three-dimensional model comprises a phase space model.

\* \* \* \* \*